US009676849B2

(12) United States Patent
Farrington et al.

(10) Patent No.: US 9,676,849 B2
(45) Date of Patent: Jun. 13, 2017

(54) ENHANCEMENT OF TRANSPORT OF THERAPEUTIC MOLECULES ACROSS THE BLOOD BRAIN BARRIER

(71) Applicant: Biogen Idec MA Inc., Cambridge, MA (US)

(72) Inventors: Graham K. Farrington, Acton, MA (US); William Sisk, Boxborough, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/370,828

(22) PCT Filed: Jan. 10, 2013

(86) PCT No.: PCT/US2013/021041
§ 371 (c)(1),
(2) Date: Jul. 7, 2014

(87) PCT Pub. No.: WO2013/106577
PCT Pub. Date: Jul. 18, 2013

(65) Prior Publication Data
US 2015/0210762 A1  Jul. 30, 2015

Related U.S. Application Data

(60) Provisional application No. 61/585,039, filed on Jan. 10, 2012.

(51) Int. Cl.
*A61K 39/00* (2006.01)
*C07K 16/28* (2006.01)
(Continued)

(52) U.S. Cl.
CPC ............ *C07K 16/28* (2013.01); *C07K 14/415* (2013.01); *C07K 14/4702* (2013.01);
(Continued)

(58) Field of Classification Search
None
See application file for complete search history.

(56) References Cited

U.S. PATENT DOCUMENTS

2009/0047300 A1* 2/2009 Abulrob et al. ........... 424/185.1
2009/0252729 A1* 10/2009 Farrington et al. ........ 424/135.1

FOREIGN PATENT DOCUMENTS

JP      2010-528588     8/2010
WO      WO 02/057445    7/2002
(Continued)

OTHER PUBLICATIONS

MetaLife "AAL58846 and AF441486" GenBank sequences published at metalife.com on Apr. 10, 2002.*
(Continued)

*Primary Examiner* — Adam M Weidner
(74) *Attorney, Agent, or Firm* — Fish & Richardson P.C.

(57) ABSTRACT

The invention is based, at least in part, on the finding that a dimeric version of a BBB-transmigrating antibody (e.g., the TMEM30A (CDC-50A) binding antibody, FC5) was found to greatly enhance transport across the BBB as compared to monovalent FC5 $V_{HH}$. The invention provides, inter alia, molecules that increase transport of pharmacologically active agents across the blood brain barrier, methods for increasing transport across the blood brain barrier, and methods of treatment of disorders or diseases having a neurological component.

42 Claims, 11 Drawing Sheets

(51) Int. Cl.
  *C07K 16/46* (2006.01)
  *C07K 14/415* (2006.01)
  *C07K 14/47* (2006.01)
(52) U.S. Cl.
  CPC .............. *C07K 16/46* (2013.01); *A61K 39/00* (2013.01); *A61K 2039/505* (2013.01); *C07K 2317/22* (2013.01); *C07K 2317/569* (2013.01); *C07K 2317/64* (2013.01); *C07K 2317/70* (2013.01); *C07K 2317/92* (2013.01); *C07K 2317/94* (2013.01); *C07K 2319/00* (2013.01); *C07K 2319/30* (2013.01); *C07K 2319/33* (2013.01)

(56) References Cited

FOREIGN PATENT DOCUMENTS

| WO | 2007/036021 | 4/2007 |
|---|---|---|
| WO | WO 2007/095338 | 8/2007 |
| WO | WO 2008/143954 | 11/2008 |
| WO | 2011/107507 | 9/2011 |
| WO | 2011/127580 | 10/2011 |

OTHER PUBLICATIONS

International Preliminary Report on Patentability in International Application No. PCT/US2013/021041, dated Jul. 15, 2014, 11 pages.
Abulrob et al., "Single Domain Antibodies as Blood-Brain Barrier Delivery Vectors", International Congress Series, Elsevier. 1277:212-223 (2005).
By et al., "Intracerebroventricular injection of an agonist-like monoclonal antibody to adenosine $A_{2A}$ receptor has antinociceptive effects in mice", Journal of Neuroimmunology, 230:178-182 (2011).
International Search Report for PCT/US2013/021041 dated Sep. 16, 2013.
Yu et al., "Boosting brain uptake of a therapeutic antibody by reducing its affinity for a transcytosis target" Science/Science Translational Medicine, Washington, DC: AAAS, US, 3(84):1-8; XP008148394 (2011).
Jain et al., "Engineering antibodies for clinical applications," Trends in Biotechnology, 25(7):308-316 (2007).
Wesolowski et al., "Single domain antibodies: promising experimental and therapeutic tools in infection and immunity," Medical Microbiology and Immunology 198(3):157-174 (2009).

* cited by examiner

```
                        SEQUENCE LISTING

<160> NUMBER OF SEQ ID NOS: 14

<210> SEQ ID NO 1
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser Ala Glu Pro Lys Ser Cys
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Ala Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320
```

```
Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 2
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Ala Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Asp Val Gln Leu
225                 230                 235                 240

Gln Ala Ser Gly Gly Gly Leu Val Gln Ala Gly Gly Ser Leu Arg Leu
                245                 250                 255

Ser Cys Ala Ala Ser Gly Phe Lys Ile Thr His Tyr Thr Met Gly Trp
            260                 265                 270

Phe Arg Gln Ala Pro Gly Lys Glu Arg Glu Phe Val Ser Arg Ile Thr
        275                 280                 285

Trp Gly Gly Asp Asn Thr Phe Tyr Ser Asn Ser Val Lys Gly Arg Phe
290                 295                 300

Thr Ile Ser Arg Asp Asn Ala Lys Asn Thr Val Tyr Leu Gln Met Asn
305                 310                 315                 320
```

```
Ser Leu Lys Pro Glu Asp Thr Ala Asp Tyr Tyr Cys Ala Ala Gly Ser
            325                 330                 335

Thr Ser Thr Ala Thr Pro Leu Arg Val Asp Tyr Trp Gly Lys Gly Thr
            340                 345                 350

Gln Val Thr Val Ser Ser
            355

<210> SEQ ID NO 3
<211> LENGTH: 358
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Ala Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Asp Val Gln Leu
225                 230                 235                 240

Gln Ala Ser Gly Gly Gly Leu Val Gln Ala Gly Gly Ser Leu Arg Leu
                245                 250                 255

Ser Cys Ala Ala Ser Gly Phe Lys Ile Thr His Tyr Thr Met Gly Trp
            260                 265                 270

Phe Arg Gln Ala Pro Gly Lys Glu Arg Glu Phe Val Ser Arg Ile Thr
        275                 280                 285

Trp Gly Gly Asp Asn Thr Phe Tyr Ser Asn Ser Val Lys Gly Arg Phe
    290                 295                 300

Thr Ile Ser Arg Asp Asn Ala Lys Asn Thr Val Tyr Leu Gln Met Asn
```

```
                305                 310                 315                 320
Ser Leu Lys Pro Glu Asp Thr Ala Asp Tyr Tyr Cys Ala Ala Asp Ala
                    325                 330                 335

Gly Ser Thr Gly Ser Tyr Gly Ser Phe Asp Tyr Trp Gly Lys Gly Thr
                340                 345                 350

Gln Val Thr Val Ser Ser
        355

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Lys Asn Ser Ser Met Ile Ser Asn Thr Pro
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Gln Ser Leu Gly Thr Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Gln Asn Leu Ser Asp Gly Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gln Asn Ile Ser Asp Gly Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ile Ser Ser His Leu Gly Gln
```

<210> SEQ ID NO 9
<211> LENGTH: 360
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

Met Ala Met Asn Tyr Asn Ala Lys Asp Glu Val Asp Gly Gly Pro Pro
1               5                   10                  15

Cys Ala Pro Gly Gly Thr Ala Lys Thr Arg Arg Pro Asp Asn Thr Ala
            20                  25                  30

Phe Lys Gln Gln Arg Leu Pro Ala Trp Gln Pro Ile Leu Thr Ala Gly
        35                  40                  45

Thr Val Leu Pro Ile Phe Phe Ile Ile Gly Leu Ile Phe Ile Pro Ile
    50                  55                  60

Gly Ile Gly Ile Phe Val Thr Ser Asn Asn Ile Arg Glu Ile Glu Ile
65                  70                  75                  80

Asp Tyr Thr Gly Thr Glu Pro Ser Ser Pro Cys Asn Lys Cys Leu Ser
                85                  90                  95

Pro Asp Val Thr Pro Cys Phe Cys Thr Ile Asn Phe Thr Leu Glu Lys
            100                 105                 110

Ser Phe Glu Gly Asn Val Phe Met Tyr Tyr Gly Leu Ser Asn Phe Tyr
        115                 120                 125

Gln Asn His Arg Arg Tyr Val Lys Ser Arg Asp Asp Ser Gln Leu Asn
    130                 135                 140

Gly Asp Ser Ser Ala Leu Leu Asn Pro Ser Lys Glu Cys Glu Pro Tyr
145                 150                 155                 160

Arg Arg Asn Glu Asp Lys Pro Ile Ala Pro Cys Gly Ala Ile Ala Asn
                165                 170                 175

Ser Met Phe Asn Asp Thr Leu Glu Leu Phe Leu Ile Gly Asn Asp Ser
            180                 185                 190

Tyr Pro Ile Pro Ile Ala Leu Lys Lys Lys Gly Ile Ala Trp Trp Thr
        195                 200                 205

Asp Lys Asn Val Lys Phe Arg Asn Pro Pro Gly Gly Asp Asn Leu Glu
    210                 215                 220

Glu Arg Phe Lys Gly Thr Thr Lys Pro Val Asn Trp Leu Lys Pro Val
225                 230                 235                 240

Tyr Met Leu Asp Ser Asp Pro Asp Asn Asn Gly Phe Ile Asn Glu Asp
                245                 250                 255

Phe Ile Val Trp Met Arg Thr Ala Ala Leu Pro Thr Phe Arg Lys Leu
            260                 265                 270

Tyr Arg Leu Ile Glu Arg Lys Ser Asp Leu His Pro Thr Leu Pro Ala
        275                 280                 285

Gly Arg Tyr Ser Leu Asn Val Thr Tyr Asn Tyr Pro Val His Tyr Phe
    290                 295                 300

Asp Gly Arg Lys Arg Met Ile Leu Ser Thr Ile Ser Trp Met Gly Gly
305                 310                 315                 320

Lys Asn Pro Phe Leu Gly Ile Ala Tyr Ile Ala Val Gly Ser Ile Ser
                325                 330                 335

Phe Leu Leu Gly Val Val Leu Val Ile Asn His Lys Tyr Arg Asn
            340                 345                 350

```
Ser Ser Asn Thr Ala Asp Ile Thr
        355                 360

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 11

Ala Leu Ala Leu
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Glu Gln Lys Leu Ile Ser Glu Glu Asp Leu
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 14

His His His His His
1               5
```

ENHANCEMENT OF TRANSPORT OF THERAPEUTIC MOLECULES ACROSS THE BLOOD BRAIN BARRIER

SEQUENCE LISTING

The instant application contains a Sequence Listing which has been submitted electronically in ASCII format and is hereby incorporated by reference in its entirety. Said ASCII copy, created on Sep. 22, 2015, is named 13751-0175US1_SL.txt and is 16,344 bytes in size.

BACKGROUND OF THE INVENTION

The distribution of macromolecules throughout the body is generally diffusion mediated with macromolecules in the blood diffusing into the tissues across highly fenestrated endothelial cell linings of the capillary vasculature. Free diffusion of macromolecules does not exist in the highly vascularized brain. Brain capillary endothelial cells lack the fenestrations seen in the rest of the circulatory system and have highly specialized endothelial cell tight intracellular junctions. These tight junctions serve to prevent the free diffusion of molecules of greater than 400 kDa from the luminal to the abluminal side of the capillary. In addition, the capillaries contain various transporter systems such as the Organic Anion Transporters (OATS) and Multi-Drug Resistance (MDR) systems that actively establish transportation gradients of molecules that might otherwise diffuse through endothelial cells. The combination of the restrictive barriers prevents the entrance of adventitious agents, including toxins and viruses for example, as well as restricting the diffusion of therapeutic entities. In addition these restrictive blood brain barriers (BBB) effectively block the passive delivery of potentially therapeutic proteins, peptides and small molecules into the brain parenchyma at pharmacologically therapeutic doses.

One successful strategy to achieve transport of therapeutic molecules across the BBB endothelial cells has been to take advantage of receptor mediated transcytosis (RMT). This strategy uses antibodies or molecules that bind specifically to proteins on BBB endothelial cells that are typically involved in the transport of molecules across the BBB endothelial cells. Such antibodies are used as shuttle molecules to deliver attached payloads while undergoing transcytosis across the BBB endothelial cells. Examples of the applications of this technology include the use of antibodies to the transferrin receptor and insulin receptors (Yu et al. 2011. Science Translational Medicine. Volume 3). In these two cases RMT antibodies were fused C-terminally to therapeutic protein domains and have been shown to transport molecules across the BBB. Unfortunately, commonly used RMT targets transferrin and insulin receptors are highly and broadly expressed in numerous tissues. This broad target expression results in a short circulating half-life, that in turn limits the time of exposure to BBB endothelial cells and thereby the dosing of the molecule into the brain. In addition, these antibodies target metabolically critical cellular functions thereby creating a potential safety risk.

Improved targeting moieties that make use of active BBB transport molecules to cross the BBB e.g., binding sites derived from antibody molecules that transmigrate across the BBB, would be of great benefit for the delivery of therapeutics into the brain.

SUMMARY OF THE INVENTION

The invention is based, at least in part, on the finding that a fusion protein comprising a blood brain barrier (BBB) transmigrating antibody, e.g., aTMEM30A (CDC-50A) binding antibody (such as, e.g., the single domain antibody FC5) was found to greatly enhance transport across the BBB as compared to monovalent $V_{HH}$. Initial binding and BBB endothelial transport experiments showed that FC5, a llama single domain $V_{HH}$ antibody (sdAb), could facilitate transport across a BBB endothelial cell layer (see, e.g., U.S. Pat. No. 7,943,129). The circulating half-life of a $V_{HH}$ is known to be short due to the low molecular weight and lack of an Fc domain (Jain, M., Kamal, N., and Batra, S. K. (2007) *Trends in biotechnology* 25(7), 307-316; Batra, S. K., Jain, M., Wittel, U. A., Chauhan, S. C., and Colcher, D. (2002) *Current opinion in biotechnology* 13(6), 603-608) Surprisingly, the circulating half-life of this construct was greatly enhanced by fusing a BBB-transmigrating single domain antibody to the N-terminus of a human Fc resulting in a divalent antibody like construct. The incorporation of such a binding site into an Fc construct creates a divalent molecule, with the potential for divalent binding each binding moiety bound to the putative target, e.g., TMEM30A, expressed on the cellular surface. Divalent binding can drive a significant change in the apparent binding affinity due to an avidity effect (Reynolds, J. A. (1979) *Biochemistry* 18(2), 264-269; Hubble, J. (1999) *Molecular immunology* 36(1), 13-18). As demonstrated herein, the affinity of the interaction was increased. Given this affinity increase, the finding that the addition of Fc to form a divalent molecule significantly increased transport across the BBB was not expected. The increased transport was not expected because, although the addition of an Fc domain can extend beta-phase pharmacokinetics owing to increased mass preventing kidney filtration of the molecule and promotion of antibody recycling in vivo by binding to FcRn, the enhanced apparent affinity increase could also have had the opposite effect owing to the elimination of circulating binding molecules upon binding to a highly expressed target. Most surprisingly however, as demonstrated herein, it was found that fusion proteins in the binding site-Fc conformation (from amino to carboxy terminus, i.e., the binding site fused to the N-terminus of Fc) had higher activity than those in the Fc-binding site conformation (binding site fused to the C-terminus of Fc). This was true despite the fact that the Fc-binding site fusion proteins (binding site fused to the C-terminus of Fc) displayed increased binding to endothelial cells in initial experiments done in vitro. Monovalent versions of the binding site-Fc constructs are also provided.

Accordingly, in one aspect, the invention pertains to a binding molecule comprising at least one pharmacologically active agent and at least one binding site, e.g., a BBB transmigrating binding site, that binds to TMEM30A, wherein the at least one binding site that binds to TMEM30A is fused i) directly or ii) via an intervening amino acid sequence to the N-terminus of an Fc moiety.

In one embodiment, the binding molecule comprises at least two binding sites.

In one embodiment, the at least one binding site comprises the FC5 amino acid sequence. In one embodiment, the binding molecule comprises at least two or at least three (e.g., two or three) binding sites that bind to TMEM30A. In one embodiment, the binding molecule comprises at least three or at least four (e.g., three or four) binding sites that bind to TMEM30A.

In one embodiment, the at least one BBB transmigrating site (e.g., binding site derived from antibody molecules that transmigrate across the BBB) is genetically fused directly to the Fc moiety.

In one embodiment, the at least one BBB transmigrating site (e.g., binding site derived from antibody molecules that transmigrate across the BBB) is genetically fused to the Fc moiety via an intervening amino acid sequence comprising a peptide linker.

In one embodiment, the at least one BBB transmigrating site (e.g., binding site derived from antibody molecules that transmigrate across the BBB) is genetically fused to the Fc moiety via an intervening amino acid sequence consisting of a peptide linker.

In one embodiment, two BBB transmigrating sites (e.g., binding sites derived from antibody molecules that transmigrate across the BBB) are fused to the N terminus of two different Fc moieties of a complete Fc region via an amino acid sequence comprising a peptide linker.

In one embodiment, the at least one BBB transmigrating site (e.g., binding site derived from antibody molecules that transmigrate across the BBB) is fused to the N terminus of an scFc molecule.

In one embodiment, the at least one pharmacologically active agent is fused to the C-terminus of the Fc region.

In one embodiment, the at least one pharmacologically active agent is a small chemical entity.

In one embodiment, the small chemical entity is fused to the binding molecule at a cysteine residue. In one embodiment, the cysteine residue is an engineered cysteine residue.

In one embodiment, the at least one pharmacologically active agent is a polypeptide.

In one embodiment, the at least one pharmacologically active agent comprises an antigen binding site (e.g., an antigen binding site derived from a non-BBB transmigrating antibody).

In one embodiment, the pharmacologically active agent is selected from the group consisting of an scFv molecule, a Fab molecule, and a single domain antibody.

In one embodiment, the at least one pharmacologically active agent is genetically fused to the binding molecule.

In one embodiment, the at least one pharmacologically active agent is covalently linked to the binding molecule.

In one embodiment, the BBB transmigrating site is genetically fused via an intervening amino acid sequence comprising the VH domain of an antibody molecule.

In one embodiment, the BBB transmigrating site is genetically fused via an intervening amino acid sequence comprising the VL domain of an antibody molecule.

In one embodiment, at least one BBB transmigrating site is genetically fused to the N terminus of a VH domain of an intact antibody molecule.

In one embodiment, at least one BBB transmigrating site is genetically fused to the N terminus of a VL domain of an intact antibody molecule.

In one embodiment, two BBB transmigrating sites are genetically fused to the N terminus of a VH domain and a VL domain of an intact antibody molecule.

In one embodiment, the intervening amino acid sequence further comprises a peptide linker.

In one embodiment, the pharmaceutically active agent is selected from the group consisting of: a neuroactive peptide, a small chemical entity, and a variable region of an antibody that binds to a target in the central nervous system.

In one embodiment, the invention pertains to a method of treating a neurological disorder, comprising administering the binding molecule of the invention to a subject.

In one embodiment, the neurological disorder is a storage disorder. In one embodiment, the neurological disorder is chronic pain. In one embodiment, the neurological disorder is epilepsy. In one embodiment, the neurological disorder is multiple sclerosis. In one embodiment, the neurological disorder is disease proteinopothy. In one embodiment, the disorder is a demyelinating disorder.

In another embodiment, the invention pertains to the use of a binding molecule of the invention in the manufacture of a medicament for treatment of a neurological disorder.

Figure 1:
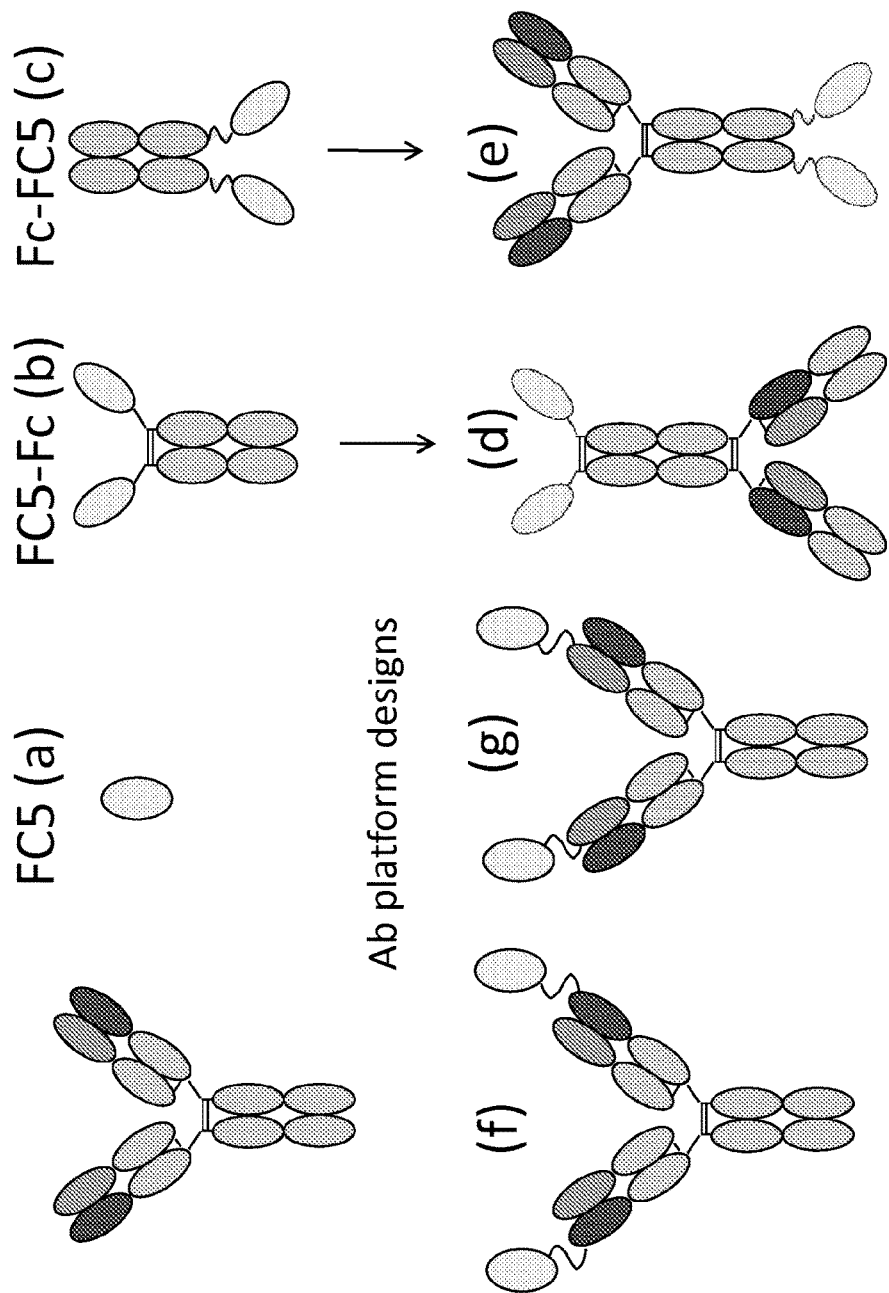
FIG. 1 shows diagrammatic representations of FC5 single heavy domain antibody (a) alone, (b) fused either N-terminally (FC5-Fc) or (c) C-terminally (Fc-FC5) to a human IgG1 agly Fc domain as well as possible antibody-like constructs which incorporate a non-BBB transmigrating domain as a pharmaceutically active moiety (d, e). Molecules (f) and (g) illustrate the addition of and FC5 single heavy domain antibody to a complete antibody molecule; the single heavy domain antibody can be fused, e.g., to the VL or VH domain, or both.

Rats at time 0 were dosed IV with a single concentration of FC5-Fc-Dal or Fc-Dal at 0.5, 2.5 or 6.0 mpk. Data is presented in panels 7a and 7b as percent maximum possible effect (MPE) at the time given or in panels 7c and 7d as percent area under the curve.

DETAILED DESCRIPTION OF THE INVENTION

A fusion protein comprising at least one BBB transmigrating single domain antibody, e.g., which binds to TMEM30A (CDC-50A) (such as, an FC5 single domain) was found to greatly enhance transport across the BBB as compared to the monovalent $V_{HH}$. In particular, the binding site-Fc conformation (from amino to carboxy terminus) demonstrated enhanced activity. Based, at least in part, on this significantly increased transport, molecules with increased transport across the blood brain barrier, methods for increasing transport across the blood brain barrier, and methods of treatment using such molecules are described herein.

Before further description of the invention, for convenience, certain terms are described below:

I. Definitions

As used herein, the term "protein" or "polypeptide" refers to a polymer of two or more of the natural amino acids or non-natural amino acids.

The term "amino acid" includes alanine (Ala or A); arginine (Arg or R); aspar-agine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, omithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" include amino acids that can have non-zero net charge on their side chains (e.g. R, K, H, E, D). These amino acids can participate in hydrophobic interactions and electrostatic interactions.

As used herein the term "linker peptide" refers to amino acid sequences that connect or link two polypeptide sequences, e.g., that link two polypeptide domains, which amino acid sequences do not naturally connect or link the two polypeptide domains in nature. In one embodiment, a linker peptide is synthetic. As used herein the term "synthetic" refers to amino acid sequences that are not naturally occurring.

Linker peptides of the invention connect two amino acid sequences via peptide bonds. In one embodiment, a linker peptide connects a BBB transmigrating moiety to a second moiety, e.g., an Fc moiety domain or region. In one embodiment, a linker peptide of the invention connects a pharmacologically active moiety to a second moiety in a linear sequence, e.g., a second moiety which is a BBB transmigrating moiety or an Fc moiety domain or region. In another embodiment, a linker peptide connects two pharmacologically active moieties. In one embodiment, a linker peptide connects or genetically fuses one or more Fc moieties domains or regions to a non-Fc moiety.

In the context of polypeptides, a "linear sequence" or a "sequence" is the order of amino acids in a polypeptide in an amino to carboxyl terminal direction in which residues that neighbor each other in the sequence are contiguous in the primary structure of the polypeptide.

As used herein, the terms "linked," "fused", or "fusion", are used interchangeably. These terms refer to the joining together of two more elements or components, by whatever means including chemical conjugation or recombinant means. As used herein, the term "covalently fused" or "covalently coupled" means that the specified moieties are either directly covalently bonded to one another, or else are indirectly covalently joined to one another through an intervening moiety or moieties, such as a linking peptide or moiety. In a preferred embodiment, moieties are covalently fused. One type of covalent linkage is a peptide bond. Methods of chemical conjugation (e.g., using heterobifunctional crosslinking agents) are known in the art. Fused moieties may also be genetically fused. As used herein, the term "genetically fused," "genetically linked" or "genetic fusion" refers to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

The subject polypeptides comprise at least one pharmacologically active moiety. A pharmacologically active moiety refers to a moiety capable of performing an action or a reaction in a biological context. For example, the term "pharmacologically active moiety" refers to pharmacologically active molecules or portions thereof which bind to components of a biological system (e.g., proteins in biological fluid or on the surface of cells or in cellular matrix) and which binding results in a biological effect (e.g., as measured by a change in the active moiety and/or the component to which it binds (e.g., a cleavage of the active moiety and/or the component to which it binds, the transmission of a signal, or the augmentation or inhibition of a biological response in a cell or in a subject)). Preferred pharmaceutically active moieties are therapeutic moieties.

Exemplary pharmacologically active moieties may comprise, e.g., a drug, an antigen binding fragment of an antibody molecule or portion thereof (e.g., F(ab), scFv, a VH domain, or a VL domain) (e.g., to impart, induce or block a biological response), a ligand binding portion of a receptor or a receptor binding portion of a ligand, an enzyme, etc. In one embodiment, a pharmacologically active moiety comprises the mature form of a protein. In another embodiment, a pharmacologically active moiety comprises a portion of a full length protein which retains biological activity. Other exemplary pharmacologically active moieties include therapeutically useful amino acids, peptides, proteins, nucleic acids, including but not limited to polynucleotides, oligonucleotides, carbohydrates and lipids. Exemplary pharmacologically active moieties of the present invention include neurotrophic factors, growth factors, enzymes, antibodies, neurotransmitters, neuromodulators, antibiotics, antiviral agents, antifungal agents, imaging or detectable agents, isotopes, and chemotherapeutic agents, and the like. The pharmacologically active moieties of the present invention also include drugs, prodrugs and precursors that can be activated when the therapeutic agent is delivered to the target tissue. The term "pharmacologically active moieties" is not meant to include a BBB transmigrating moiety. Pharmacologically active agents are non-BBB transmigrating moieties.

The binding molecules of the invention are "chimeric" or "fusion" proteins. Such proteins comprises a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created using methods well known in the art, for example, by chemical synthesis, or by creating and translating a polynucleotide in which the peptide regions are encoded in the desired relationship.

Polypeptides of the invention are binding molecules, i.e., that comprise binding domains or binding sites derived from BBB-transmigrating antibodies. A BBB transmigrating antibody facilitates transmigration of a moiety attached thereto across the BBB. Exemplary BBB transmigrating antibody binding sites are described in U.S. Pat. No. 7,943,129. In one embodiment, a BBB transmigrating antibody binds to TMEM30A. The terms "binding domain" or "binding site", as used herein, refer to the portion, region, or site of polypeptide that mediates specific binding with a target molecule (e.g. a TMEM30A binding site or other site that facilitates BBB transmigration). Exemplary binding domains include an antigen binding site (e.g., a VH and/or VL domain) or molecules comprising such a binding site (e.g., an antibody or a single domain antibody).

Polypeptides of the invention are monovalent or multivalent with respect to the BBB transmigrating moiety, e.g., comprise at least 1, 2, 3, 4, 5 or more BBB transmigrating moieties.

Pharmacologically active moieties as described herein may also include binding domains or binding sites, e.g., as derived from an antibody molecule (e.g., a VH and/or VL domain from an antibody that does not transmigrate across the BBB), molecules comprising such a binding site (e.g., an antibody or single domain antibody), a receptor binding domain of a ligand, a ligand binding domain of a receptor or a catalytic domain. The term "ligand binding domain" as used herein refers to a native receptor (e.g., cell surface receptor) or a region or derivative thereof retaining at least a qualitative ligand binding ability, and preferably the biological activity of the corresponding native receptor. The term "receptor binding domain" as used herein refers to a native ligand or region or derivative thereof retaining at least a qualitative receptor binding ability, and preferably the biological activity of the corresponding native ligand.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens e.g., to TMEM30A and a therapeutically relevant target binding site) joined to Fc moieties, domains, regions or scFc regions.

As used herein, the term "Fc region" shall be defined as the portion of a polypeptide which corresponds to the Fc region of native immunoglobulin, i.e., as formed by the dimeric association of the respective Fc domains (or Fc moieties) of its two heavy chains. A native Fc region is homodimeric and comprises two polypeptide chains. In contrast, the term "genetically-fused Fc region" or "single-chain Fc region" (scFc region), as used herein, refers to a synthetic dimeric Fc region comprised of Fc domains (or Fc moieties) genetically linked within a single polypeptide chain (i.e., encoded in a single contiguous genetic sequence) as described, e.g., in U.S. application 20110243966. In one embodiment, when an scFc region is used, the binding molecule is monovalent with respect to the BBB transmigrating moiety.

As used herein, the term "Fc domain" refers to the portion of a single immunoglobulin heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain. As used herein, the term "Fc region" refers to dimerized Fc domains which resemble the Fc region of native antibodies (e.g., whether made in the traditional two polypeptide chain format or as a single chain Fc region).

As used herein, the term "Fc domain portion" or "Fc moiety" includes an amino acid sequence of an Fc domain or derived from an Fc domain. In certain embodiments, an Fc moiety comprises at least one of: a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In one embodiment, a binding molecule of the invention comprises a complete Fc region, whether present as one polypeptide chain (an scFc molecule) or in the wildtype form as two polypeptide chains.

Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In one embodiment, an Fc moiety of the invention comprises at least the portion of an Fc molecule known in the art to be required for FcRn binding, referred to herein as a neonatal receptor (FcRn) binding partner. An FcRn binding partner is a molecule or portion thereof that can be specifically bound by the FcRn receptor with consequent active transport by the FcRn receptor of the FcRn binding partner.

FcRn binding partners of the present invention encompass molecules that can be specifically bound by the FcRn receptor including whole IgG, the Fc fragment of IgG, and other fragments that include the complete binding region of the FcRn receptor. In another embodiment, an Fc moiety domain or region of a binding molecule of the invention is modified so that it exhibits reduced, minimal, or no binding to FcRn. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238.

Certain of the above mutations may confer new functionality upon the Fc moiety. For example, one embodiment incorporates N297A, removing a highly conserved N-glycosylation site. The effect of this mutation is to reduce glycosylation, thereby reducing effector function and/or immunogenicity. As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591).

In one embodiment, the FcRn binding partner is a polypeptide including the sequence PKNSSMISNTP (SEQ ID NO: 4) and optionally further including a sequence selected from HQSLGTQ (SEQ ID NO: 5), HQNLSDGK (SEQ ID NO: 6), HQNISDGK (SEQ ID NO: 7), or VISSHLGQ (SEQ ID NO: 8) (U.S. Pat. No. 5,739,277).

Those skilled in the art will be familiar with many other Fc mutants or analogs thereof which exhibit altered effector function and/or FcRn binding. In addition, means of chemically modifying immunoglobulin constant regions (e.g. pegylated), or fragments thereof (see, e.g., Aslam and Dent 1998, Bioconjugation: Protein Coupling Techniques For the Biomedical Sciences Macmilan Reference, London) are well known in the art, for example, in U.S. application 20120003210.

In one embodiment, an Fc moiety, domain or region to which a BBB transmigrating moiety is attached is aglycosylated using methods known in the art, e.g., by mutating residues which are normally glycosylated or by altering the expression of the polypeptide so that glycosylation does not occur. As an example, one specific embodiment, incorporates the N297A mutation, removing a highly conserved N-glycosylation site. In another embodiment, an Fc moiety incorporates a mutation at position 299, e.g., a T299 mutation to another amino acid as described in U.S. Pat. No. 7,863,419. In addition to alanine other amino acids may be substituted for the wildtype amino acids at the positions specified above or known in the art to reduce Fc function.

In another embodiment, mutations disclosed in Armour, K. L., Clark, M. R., Hadley, A. G. & Williamson L. M. (1999), Eur J Immunol 29: 2613-2624 may be introduced into the subject binding molecules.

Mutations may be introduced singly into Fc giving rise to more than one hundred Fc moieties distinct from native Fc. Additionally, combinations of two, three, or more of these individual mutations may be introduced together, giving rise to hundreds more potential Fc regions. Moreover, one of the Fc moieties of a construct of the invention may be mutated and the other Fc moiety not mutated at all, or they both may be mutated but with different mutations.

Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display or via chemical library screening (see, e.g., McCafferty et al. 1990, Nature 348:552, Kang et al. 1991, Proc. Natl. Acad. Sci. USA 88:4363; EP 0 589 877 B1).

In another embodiment, an Fc region of the invention (e.g., an scFc region) comprises at least the portion of an Fc molecule known in the art to be required for FcγR binding.

In one embodiment, an Fc region of the invention (e.g., an scFc region) comprises at least the portion of an Fc molecule known in the art to be required for Protein A binding. In one embodiment, an Fc region of the invention (e.g., an scFc region) comprises at least the portion of an Fc molecule known in the art to be required for protein G binding. In one embodiment, such a molecule does not bind to FcRn.

As set forth herein, it will be understood by one of ordinary skill in the art that an Fc domain may also be modified by including one or more amino acid changes (substitutions, additions or deletions) such that it varies in amino acid sequence from a wild type Fc moiety. Many such changes or alterations are known in the art. In certain exemplary embodiments, the Fc moiety retains an effector function (e.g., FcγR binding) and in certain embodiments, the Fc moiety lacks or has reduced effector function.

The Fc domains or moieties of a polypeptide of the invention may be from any isotype (A, E, G, or M) and may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

Polypeptides comprising the linker peptides of the invention can be made using techniques that are known in the art. In one embodiment, the polypeptides of the invention are "recombinantly produced," i.e., are produced using recombinant DNA technology. Exemplary techniques for making the polypeptides of the invention are set forth in more detail herein.

As used herein, the term "pharmaceutically acceptable carrier" means a chemical composition or compound with which an active ingredient may be combined and which, following the combination, can be used to administer the active ingredient to a subject. As used herein, the term "physiologically acceptable" ester or salt means an ester or salt form of the active ingredient which is compatible with any other ingredients of the pharmaceutical composition, which is not deleterious to the subject to which the composition is to be administered. As used herein, "pharmaceutically acceptable carrier" also includes, but is not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

As used herein, "an effective amount" is an amount sufficient to produce a therapeutic response.

As used herein, the term "proteinopathy" refers to disorders characterized by misfolded proteins or aggregated proteins which disorders have a genetic component.

II. BBB Transmigrating Antibodies

In one embodiment, a BBB transmigrating moiety is as described in U.S. Pat. No. 7,943,129. For example, in one embodiment, a BBB transmigrating moiety comprises an amino acid sequence set forth in a sequence selected from the group consisting of SEQ ID NO:85, SEQ ID NO:86 (FC44), and SEQ ID NO:87 (FC7) as set forth in U.S. Pat. No. 7,943,129. In one embodiment, a BBB transmigrating moiety is an FC5 moiety. FC5 is a heavy chain antibody (HCA, also referred to as two-chain, two-chain heavy chain antibody, $V_{HH}$, or single domain antibody) derived from a camelid. Compared with conventional four-chain immunoglobulins of IgG-type, which are also produced by camelids, these antibodies lack the light chains and CH1 domains of conventional immunoglobulins. One of the salient features of these naturally occurring heavy chain antibodies is the predominant presence of Glu, Arg and Gly at VL interface positions 44, 45 and 47 (Kabat numbering), respectively, of their variable domain (designated $V_{HH}$). The same positions in the variable domain of the heavy chain of conventional four-chain antibodies (designated VH) are almost exclusively occupied by Gly, Leu and Trp. These differences are thought to be responsible for the high solubility and stability of camelid HCA variable domain ($V_{HH}$), as compared with the relative insolubility of VH domain of the conventional four-chain antibodies. Two more key features of camelid $V_{HH}$ domains are their comparatively longer CDR3 and high incidence of cysteine pairs in CDRs. It appears that cysteine pairs mediate the formation of a disulfide bridge and are therefore involved in modulating the surface topology of the antibody combining site. In the crystal structure of a camel sdAb-lysozyme complex, a rigid loop protruding from the sdAb and partly stabilized by a CDR disulfide linkage extends out of the combining site and penetrates deeply into the lysozyme active site (Desmyter et al., Nature Struct. Biol., 3, 803-811 (1996)).

In one embodiment, a BBB transmigrating antibody binds to TMEM30A (C6orf67, CDC50A). Exemplary moieties which bind to TMEM30A are known or can be made using methods well known in the art. For example, an amino acid sequence comprising the amino acid sequence of TMEM30A or a portion thereof can be used to make antibodies that specifically recognize the TMEM30A amino acid sequence or to screen for binding moieties which specifically bind to TMEM30A from a library of binding sites. Binding sites from such antibodies or derived from libraries can be used in a binding molecule of the invention. The amino acid sequence of TMEM30A (SEQ ID NO: 9) is shown below:

```
         10         20         30         40         50         60
MAMNYNAKDE VDGGPPCAPG GTAKTRRPDN TAFKQQRLPA WQPILTAGTV LPIFFIIGLI 70         80         90        100        110        120
FIPIGIGIFV TSNNIREIEI DYTGTEPSSP CNKCLSPDVT PCFCTINFTL EKSFEGNVFM
```

-continued

```
        130         140         150         160         170         180
YYGLSNFYQN  HRRYVKSRDD  SQLNGDSSAL  LNPSKECEPY  RRNEDKPIAP  CGAIANSMFN 190         200         210         220         230         240
DTLELFLIGN  DSYPIPIALK  KKGIAWWTDK  NVKFRNPPGG  DNLEERFKGT  TKPVNWLKPV 250         260         270         280         290         300
YMLDSDPDNN  GFINEDFIVW  MRTAALPTFR  KLYRLIERKS  DLHPTLPAGR  YSLNVTYNYP 310         320         330         340         350         360
VHYFDGRKRM  ILSTISWMGG  KNPFLGIAYI  AVGSISFLLG  VVLLVINHKY  RNSSNTADIT
```

Polypeptides of the invention may comprise a variable region or portion thereof (e.g. a VL and/or VH domain) derived from an antibody which binds to TMEM30A using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

While the variable region may be derived from polyclonal antibodies harvested from the serum of an immunized mammal, it is often desirable to isolate individual lymphocytes from the spleen, lymph nodes or peripheral blood to provide homogenous preparations of monoclonal antibodies (MAbs) from which the desired variable region is derived. Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature,* 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the antibody genetically encoded by the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal".

Hybridoma cells thus prepared can be seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are grown is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunosorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice,* pp 59-103 (Academic Press, 1986)). It will further be appreciated that the monoclonal antibodies secreted by the subclones may be separated from culture medium, ascites fluid or serum by conventional purification procedures such as, for example, affinity chromatography (e.g., protein-A, protein-G, or protein-L affinity chromatography), hydroxylapatite chromatography, gel electrophoresis, or dialysis.

Optionally, antibodies may be screened for binding to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

DNA encoding the desired monoclonal antibody may be readily isolated and sequenced using any of the conventional procedures described supra for the isolation of constant region domain sequences (e.g., by using oligonucleotide probes that are capable of binding specifically to genes encoding the heavy and light chains of murine antibodies). The isolated and subcloned hybridoma cells serve as a preferred source of such DNA. More particularly, the isolated DNA (which may be synthetic as described herein) may be used to clone the desired variable region sequences for incorporation in the polypeptides of the invention.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific antibodies that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, variable (V) domains can be obtained from libraries of variable gene sequences from an animal of choice. Libraries expressing random combinations of domains, e.g., $V_H$ and/or $V_L$ domains, can be screened with a desired antigen to identify elements which have desired binding characteristics. Methods of such screening are well known in the art. For example, antibody gene repertoires can be cloned into a λ bacteriophage expression vector (Huse, W D et al. (1989). *Science*, 2476:1275). In addition, cells (Francisco et al. (1994), *PNAS*, 90:10444; Georgiou et al. (1997), *Nat. Biotech.*, 15:29; Boder and Wittrup (1997) *Nat. Biotechnol.* 15:553; Boder et al. (2000), *PNAS*, 97:10701; Daugtherty, P. et al. (2000) *J. Immunol. Methods.* 243:211) or viruses (e.g., Hoogenboom, H R. (1998), *Immunotechnology* 4:1; Winter et al. (1994). *Annu. Rev. Immunol.* 12:433; Griffiths, A D. (1998). *Curr. Opin. Biotechnol.* 9:102) expressing antibodies on their surface can be screened.

Those skilled in the art will also appreciate that DNA encoding antibody variable domains may also be derived from antibody libraries expressed in phage, yeast, or bacteria using methods known in the art. Exemplary methods are set forth, for example, in EP 368 684 B1; U.S. Pat. No. 5,969,108; Hoogenboom et al., (2000) *Immunol. Today* 21:371; Nagy et al. (2002) *Nat. Med.* 8:801; Huie et al. (2001), *PNAS*, 98:2682; Lui et al. (2002), *J. Mol. Biol.* 315:1063, each of which is incorporated herein by reference. Several publications (e.g., Marks et al. (1992), *Bio/Technology* 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), *PNAS* 95:14130; Hanes and Pluckthun. (1999), *Curr. Top. Microbiol. Immunol.* 243:107; He and Taussig. (1997), *Nuc. Acids Res.*, 25:5132; Hanes et al. (2000), *Nat. Biotechnol.* 18:1287; Wilson et al. (2001), *PNAS*, 98:3750; or Irving et al. (2001) *J. Immunol. Methods* 248:31).

Exemplary libraries for screening are human variable gene libraries. $V_L$ and $V_H$ domains from a non-human source may also be used. Libraries can be naïve, from immunized subjects, or semi-synthetic (Hoogenboom and Winter. (1992). *J. Mol. Biol.* 227:381; Griffiths et al. (1995) *EMBO J.* 13:3245; de Kruif et al. (1995). *J. Mol. Biol.* 248:97; Barbas et al. (1992), *PNAS*, 89:4457). In one embodiment, mutations can be made to immunoglobulin domains to create a library of nucleic acid molecules having greater heterogeneity (Thompson et al. (1996), *J. Mol. Biol.* 256:77; Lamminmaki et al. (1999), *J. Mol. Biol.* 291:589; Caldwell and Joyce. (1992), *PCR Methods Appl.* 2:28; Caldwell and Joyce. (1994), *PCR Methods Appl.* 3:S136). Standard screening procedures can be used to select high affinity variants. In another embodiment, changes to $V_H$ and $V_L$ sequences can be made to increase antibody avidity, e.g., using information obtained from crystal structures using techniques known in the art.

Another exemplary library is a camelid library which comprises single domain antibodies. Exemplary single domain molecules include an isolated heavy chain variable domain ($V_H$) of an antibody, i.e., a heavy chain variable domain, without a light chain variable domain, and an isolated light chain variable domain ($V_L$) of an antibody, i.e., a light chain variable domain, without a heavy chain variable domain. Exemplary single-domain antibodies employed in the binding molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as $V_{HH}$, forms the entire antigen-binding domain. The main differences between camelid $V_{HH}$ variable regions and those derived from conventional antibodies (VH) include (a) more hydrophobic amino acids in the light chain contact surface of VH as compared to the corresponding region in $V_{HH}$, (b) a longer CDR3 in $V_{HH}$, and (c) the frequent occurrence of a disulfide bond between CDR1 and CDR3 in $V_{HH}$. Methods for making single domain binding molecules are described in U.S. Pat. Nos 6,005,079 and 6,765,087, both of which are incorporated herein by reference. Exemplary single domain antibodies comprising $V_{HH}$ domains include Nanobodies® (Ablynx NV, Ghent, Belgium).

Moreover, variable region sequences useful for producing the polypeptides of the present invention may be obtained from a number of different sources. For example, as discussed above, a variety of human gene sequences are available in the form of publicly accessible deposits. Many sequences of antibodies and antibody-encoding genes (e.g., antibodies known to have clinically beneficial properties) have been published and suitable variable region sequences (e.g. VL and VH sequences) can be synthesized from these sequences using art recognized techniques.

In another embodiment, a binding domain of a polypeptide of the invention consists of a $V_H$ domain, e.g., derived from camelids, which is stable in the absence of a $V_L$ chain (Hamers-Casterman et al. (1993). *Nature*, 363:446; Desmyter et al. (1996). *Nat. Struct. Biol.* 3: 803; Decanniere et al. (1999). *Structure*, 7:361; Davies et al. (1996). *Protein Eng.*, 9:531; Kortt et al. (1995). *J. Protein Chem.*, 14:167).

A polypeptide of the invention may comprise a variable domain or CDR(s) derived from a fully murine, fully human, chimeric, humanized, non-human primate or primatized antibody. Non-human antibodies, or fragments or domains thereof, can be altered to reduce their immunogenicity using art recognized techniques. Humanized antibodies are antibodies derived from non-human antibodies, that have been modified to retain or substantially retain the binding properties of the parent antibody, but which are less immunogenic in humans that the parent, non-human antibodies. In the case of humanized target antibodies, this may be achieved by various methods, including (a) grafting the entire non-human variable domains onto human constant regions to generate chimeric target antibodies; (b) grafting at least a part of one or more of the non-human complementarity determining regions (CDRs) into a human framework and constant regions with or without retention of critical framework residues; (c) transplanting the entire non-human variable domains, but "cloaking" them with a human-like section by replacement of surface residues. Such methods are disclosed in Morrison et al., (1984), *PNAS*. 81: 6851-5; Morrison et al., (1988), *Adv. Immunol*. 44: 65-92; Verhoeyen et al., (1988), *Science* 239: 1534-1536; Padlan, (1991), *Molec. Immun*. 28: 489-498; Padlan, (1994), *Molec. Immun*. 31: 169-217; and U.S. Pat. Nos. 5,585,089, 5,693,761 and 5,693,762 all of which are hereby incorporated by reference in their entirety.

De-immunization can also be used to decrease the immunogenicity of a polypeptide of the invention. As used herein, the term "de-immunization" includes modification of T cell epitopes (see, e.g., WO9852976A1, WO0034317A2). For example, VH and VL sequences are analyzed and a human T cell epitope "map" from each V region showing the location of epitopes in relation to complementarity-determining regions (CDRs) and other key residues within the sequence is generated. Individual T cell epitopes from the T cell epitope map are analyzed in order to identify alternative amino acid substitutions with a low risk of altering the activity of the final antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

In one embodiment, the variable domains employed in a polypeptide of the invention are altered by at least partial replacement of one or more CDRs. In another embodiment, variable domains can optionally be altered, e.g., by partial framework region replacement and sequence changing. In making a humanized variable region the CDRs may be derived from an antibody of the same class or even subclass as the antibody from which the framework regions are derived, however, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antigen binding site with reduced immunogenicity.

FC5 is an exemplary TMEM30A binding moiety that can be incorporated into a polypeptide of the invention. The amino acid sequence of FC5 (SEQ ID NO: 10) is set forth below:

```
E V Q L Q A S G G G L V Q A G G S L R L S C A A S
G F K I T H Y T M G W F R Q A P G K E R E F V S R
I T W G G D N T F Y S N S V K G R F T I S R D N A
K N T V Y L Q M N S L K P E D T A D Y Y C A A G S
T S T A T P L R V - - - D Y W G K G T Q V T V S S
```

III. Optional Linker Peptides

The polypeptides of the invention optionally comprise at least one linker peptide. In one embodiment, two or more linker peptides are present in a polypeptide of the polypeptide of the invention. In another embodiment, a polypeptide of the invention comprises 3, 4, 5, 6, 7, 8, 9 or 10 linker peptides.

Linker peptides of the invention may occur one time at a given position, or may occur multiple times (i.e., the sequence of the linker peptide may be repeated x times in sequence) at a given position in a recombinant polypeptide. For example, in one embodiment, a linker peptide of the invention is repeated between 1 and 10 times (inclusive) at a given position in a polypeptide. In another embodiment, a linker peptide occurs 2, 3, 4, 5, 6, 7, 8, 9 or 10 times at a given position in a polypeptide.

Linker peptides of the invention can be of varying lengths. In one embodiment, a linker peptide of the invention is from about 5 to about 75 amino acids in length. In another embodiment, a linker peptide of the invention is from about 5 to about 50 amino acids in length. In another embodiment, a linker peptide of the invention is from about 10 to about 40 amino acids in length. In another embodiment, a linker peptide of the invention is from about 15 to about 35 amino acids in length. In another embodiment, a linker peptide of the invention is from about 15 to about 20amino acids in length. In another embodiment, a linker peptide of the invention is from about 15 amino acids in length.

Linker peptides are so frequently used in protein engineering that they have become standard assembly parts in synthetic biology (see e.g., Anderson, J. C., et al. Journal of Biological Engineering 2010. 4:1 and the partsregistry web site which lists standard biological parts used in genetic constructs).

Some examples of current, art recognized uses for linker peptides include uses in: scFv molecules (Freund et al. FEBS 1993. 320:97); single chain immunoglobulin molecules (Shu et al. 1993. PNAS. USA 90:7995); minibodies (Hu et al. 1996 Cancer Res. 56:3055); CH2 domain deleted antibodies (Mueller, B. M., et al. 1990 PNAS USA. 87:5702); single chain bispecific antibodies (Schlereth et al. 2005 Cancer Res. 65:2882); full-length IgG-like bispecific antibodies (Marvin, J. S. et al. 2005 Acta Pharmacol Sin 26:649 and the references cited therein as well as Michaelson, J. S., et al. 2009 MAbs. 1:128 and Orcutt K. D. et al. 2010 Protein Eng Des Sel. 23:221); scFv fusion proteins (deGraaf et al. 2002 British Journal of Cancer 86:811);

developing protein-fragment complementation assays (Remy, I. et al. 2007 BioTechiques 42:137).

Other exemplary linker peptides include those which reduce xylose (e.g., as disclosed in PCT/US11/66947) may be employed in the instant binding molecules.

Linker peptides may be attached to the N or to the C terminus (or both) of polypeptides to which they are attached.

IV. Exemplary Pharmaceutically Active Moieties

Depending on the disease or disorder or condition targeted, a variety of drug cargoes, e.g., pharmacologically active agents or, equivalently, pharmaceutically active moieties, can be delivered successfully in vivo using binding molecules of the invention, for example, binding molecules comprising the BBB transmigrating sites according to the invention, e.g., targeting TMEM30A. As used herein, the terms "pharmaceutically active moiety" and "pharmacologic compound" shall refer to any moiety or compound useful in treating or ameliorating the effects of a disease or disorder. For example, diseases or disorders including neurodegenerative diseases such as, Alzheimer's disease, Parkinson's disease, Huntington's disease, amyotrohpic lateral sclerosis (ALS, Lou Gehrig's disease), pain epilepsy, storage diseases and multiple sclerosis can be targeted.

Exemplary pharmaceutically active molecules include: nerve growth factor (NGF), brain derived neurotrophic factor (BDNF), ciliary neruotrophic factor (CNTF), glial cell-line neurotrohphic factor (GDNF) and insulin-like growth factor (IGF). In addition, other compounds that have been shown to have therapeutic potential and may be delivered by antibodies of the invention are neuropeptides, including, but not limited to, Substance P, neuropeptide Y, dalargin, alpha synuclein, vasoactive intestinal peptide (VIP), gamma-amino-butyric acid (GABA), dopamine, cholecystokinin (CCK), endorphins, enkephalins and thyrotropin releasing hormone (TRH). Further exemplary therapeutics may include cytokines, anxiolytic agents, anticonvulsants, polynucleotides and transgenes, including, for example, small-interfering RNAs which may be used for such neuronal disorders, including, but not limited to, psychiatric illnesses, such as, for example anxiety, depression, schizophrenia, and sleep disorders, as well as epilepsies, seizure disorders, stroke and cerebrovascular disorders, encephalitis and meningitis, memory and cognition disorders, acute or chronic pain (e.g., refractory) and physical trauma.

In one embodiment, a pharmaceutically active moiety comprises an antigen binding site which does not bind to TMEM30A. In certain embodiments, the polypeptides of the invention have at least one binding site specific for a non-TMEM30A target molecule which mediates a biological effect. In one embodiment, the binding site modulates cellular activation or inhibition (e.g., by binding to a cell surface receptor and resulting in transmission of an activating or inhibitory signal). In one embodiment, the binding site is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, by promoting lysis of a fibrin clot or promoting clot formation, or by modulating the amount of a substance which is bioavailable. In another embodiment, the polypeptides of the invention have at least one binding site specific for an antigen targeted for reduction or elimination, e.g., a cell surface antigen or a soluble antigen).

In yet other embodiments, a polypeptide of the invention binds to a molecule which is useful in treating a neurological disease or disorder. For example, a polypeptide may bind to an antigen present on a neural cell (e.g., a neuron, a glial cell, or a). In certain embodiments, the antigen associated with a neurological disorder may be an autoimmune or inflammatory disorder described supra. As used herein, the term "neurological disease or disorder" includes disorders or conditions in a subject wherein the nervous system either degenerates (e.g., neurodegenerative disorders, as well as disorders where the nervous system fails to develop properly or fails to regenerate following injury, e.g., spinal cord injury). Examples of neurological disorders that can be diagnosed, prevented or treated by the methods and compositions of the present invention include, but are not limited to, Multiple Sclerosis, Huntington's Disease, Alzheimer's Disease, Parkinson's Disease, neuropathic pain, traumatic brain injury, Guillain-Barré syndrome and chronic inflammatory demyelinating polyneuropathy (CIDP).

Additional exemplary pharmacologically active moieties are discussed further below:

i. Antigen Binding Portions

In certain embodiments a pharmaceutically active moiety comprises at least one antigen binding portion (binding site), e.g., of an antibody or single domain antibody. In one embodiment, the antigen binding portion targets the composition to a particular cell type or tissue.

In other embodiments, a binding site of a pharmaceutically active moiety of the invention may comprise an antigen binding portion or fragment. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, antigen binding fragments can be derived from antibodies or antibody variants described supra. Antigen binding portions can be produced by recombinant or biochemical methods that are well known in the art. Exemplary antigen-binding fragments include VH and/or VL (if either variable region alone is sufficient to bind antigen), Fv, Fab, Fab', and (Fab')$_2$.

In other embodiments, a pharmaceutically active moiety of the invention may comprise a binding site from single chain binding molecule (e.g., a single chain variable region or scFv). Techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242:1038-1041 (1988)).

In certain embodiments, a pharmaceutically active moiety of the invention comprises one or more binding sites or regions comprising or consisting of a single chain variable region sequence (scFv). Single chain variable region sequences comprise a single polypeptide having one or more antigen binding sites, e.g., a $V_L$ domain linked by a linker peptide to a $V_H$ domain. The VL and/or VH domains may be derived from antibodies known in the art or variants thereof. ScFv molecules can be constructed in a $V_H$-linker-$V_L$ orientation or $V_L$-linker-$V_H$ orientation.

In certain embodiments, a scFv molecule employed in a pharmaceutically active moiety of the invention is a stabilized scFv molecule. In one embodiment, the stabilized scFv molecule may comprise a linker peptide interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Exemplary stabilized scFv molecules which may be present in the polypeptides of the invention are described in U.S. patent application Ser. No. 11/725,970, filed on Mar. 19, 2007, each of which is incorporated herein by reference in its entirety.

In certain exemplary embodiments, the pharmaceutically active moieties of the invention comprise at least one scFv molecule that is operably linked via a linker peptide to the C-terminus and/or N-terminus of an Fc region.

In one embodiment, a pharmaceutically active moiety of the invention comprises at least one CDR from an antibody that recognizes a desired target. In another embodiment, a pharmaceutically active moiety of the present invention comprises at least two CDRs from an antibody that recognizes a desired target. In another embodiment, a pharmaceutically active moiety of the present invention comprises at least three CDRs from an antibody that recognizes a desired target. In another embodiment, a pharmaceutically active moiety of the present invention comprises at least four CDRs from an antibody that recognizes a desired target. In another embodiment, a pharmaceutically active moiety of the present invention comprises at least five CDRs from an antibody that recognizes a desired target. In another embodiment, a pharmaceutically active moiety of the present invention comprises all six CDRs from an antibody that recognizes a desired target. In one embodiment, a pharmaceutically active moiety of the invention comprises the complete amino acid sequence of an antibody molecule that recognizes a desired target (e.g., in the case of a bispecific, tetravalent antibody molecule).

Exemplary antibodies from which binding sites can be derived for use in a pharmaceutically active moiety of the invention are known in the art. For example, antibodies currently approved by the FDA for use in treatment can be used to derive binding sites. In one embodiment, an exemplary binding site is derived from an anti-Lingo antibody (see, e.g., PCT/US2008/000316).

In other aspects, a pharmaceutically active moiety of the invention may comprise a modified antibody molecule or an antigen binding site (or portions thereof) derived from a modified form of antibody. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, a pharmaceutically active moiety of the invention comprises an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, a pharmaceutically active moiety of the invention comprises a diabody which is operably linked to the N-terminus and/or C-terminus of at least one genetically-fused Fc region (i.e., scFc region).

In certain embodiments, a pharmaceutically active moiety of the invention comprises a non-BBB transmigrating antibody binding site (e.g., a non-TEME30A binding single domain binding molecule, such as a single domain antibody).

ii. Non-Immunoglobulin Binding Molecules

In certain other embodiments, a pharmaceutically active moiety of the invention comprises one or more binding sites derived from a non-immunoglobulin binding molecule. As used herein, the term "non-immunoglobulin binding molecules" are binding molecules whose binding sites comprise an amino acid sequence derived from a polypeptide other than an immunoglobulin. Examples of binding molecules comprising binding sites not derived from antibody molecules include receptor binding sites and ligand binding sites which are discussed in more detail infra.

Non-immunoglobulin pharmaceutically active moieties can comprise amino acid sequences that are derived from a member of the immunoglobulin superfamily that is not an immunoglobulin (e.g. a T-cell receptor or a cell-adhesion protein (e.g., CTLA-4, N-CAM, telokin)). In other embodiments, amino acid sequences may comprise a protein topology that is not based on the immunoglobulin fold (e.g. such as ankyrin repeat proteins or fibronectins) but which nonetheless are capable of specifically binding to a target.

Non-immunoglobulin based pharmaceutically active moieties may be identified by selection or isolation of a target-binding variant from a library of binding molecules having artificially diversified binding sites. Diversified libraries can be generated using completely random approaches (e.g., error-prone PCR, exon shuffling, or directed evolution) or aided by art-recognized design strategies. For example, amino acid positions that are usually involved when the binding site interacts with its cognate target molecule can be randomized by insertion of degenerate codons, trinucleotides, random peptides, or entire loops at corresponding positions within the nucleic acid which encodes the binding site (see e.g., U.S. Pub. No. 20040132028). The location of the amino acid positions can be identified by investigation of the crystal structure of the binding site in complex with the target molecule. Candidate positions for randomization include loops, flat surfaces, helices, and binding cavities of the binding site. In certain embodiments, amino acids within the binding site that are likely candidates for diversification can be identified by their homology with the immunoglobulin fold. For example, residues within the CDR-like loops of fibronectin may be randomized to generate a library of fibronectin binding molecules (see, e.g., Koide et al., J. Mol. Biol., 284: 1141-1151 (1998)). Other portions of the binding site which may be randomized include flat surfaces. Selection can be achieved by art-recognized methods such as phage display, yeast display, or ribosome display.

In one embodiment, a pharmaceutically active moiety of the invention comprises a binding site from a fibronectin binding molecule. Fibronectin binding molecules (e.g., molecules comprising the Fibronectin type I, II, or III domains) display CDR-like loops which, in contrast to immunoglobulins, do not rely on intra-chain disulfide bonds. Methods for making fibronectin polypeptides are described, for example, in WO 01/64942 and in U.S. Pat. Nos. 6,673,901, 6,703,199, 7,078,490, and 7,119,171, which are incorporated herein by reference. In one exemplary embodiment, the fibronectin polypeptide is AdNectin® (Adnexus Therpaeutics, Waltham, Mass.).

In another embodiment, a pharmaceutically active moiety of the invention comprises a binding site from an Affibody® (Abcam, Cambridge, Mass.). Affibodies are derived from the immunoglobulin binding domains of staphylococcal Protein A (SPA) (see e.g., Nord et al., Nat. Biotechnol., 15: 772-777 (1997)). Methods for making affibody binding sites are described in U.S. Pat. Nos. 6,740,734 and 6,602,977 and in WO 00/63243, each of which is incorporated herein by reference.

In another embodiment, a pharmaceutically active moiety of the invention comprises a binding site from an Anticalin® (Pieris AG, Friesing, Germany). Anticalins (also known as lipocalins) are members of a diverse β-barrel protein family whose function is to bind target molecules in their barrel/loop region. Lipocalin binding sites may be engineered by randomizing loop sequences connecting the strands of the barrel (see e.g., Schlehuber et al., Drug Discov. Today, 10: 23-33 (2005); Beste et al., PNAS, 96: 1898-1903 (1999). Anticalin binding sites employed in the binding molecules of the invention may be obtainable starting from polypeptides of the lipocalin family which are mutated in four segments that correspond to the sequence positions of the linear polypeptide sequence comprising amino acid positions 28 to 45, 58 to 69, 86 to 99 and 114 to 129 of the Bilin-binding protein (BBP) of *Pieris brassica*. Other methods for making anticalin binding sites are described in WO99/16873 and WO 05/019254, each of which is incorporated herein by reference.

In another embodiment, a pharmaceutically active moiety of the invention comprises a binding site from a cysteine-rich polypeptide. Cysteine-rich domains employed in the practice of the present invention typically do not form a α-helix, a β sheet, or a β-barrel structure. Typically, the disulfide bonds promote folding of the domain into a three-dimensional structure. Usually, cysteine-rich domains have at least two disulfide bonds, more typically at least three disulfide bonds. An exemplary cysteine-rich polypeptide is an A domain protein. A-domains (sometimes called "complement-type repeats") contain about 30-50 or 30-65 amino acids. In some embodiments, the domains comprise about 35-45 amino acids and in some cases about 40 amino acids. Within the 30-50 amino acids, there are about 6 cysteine residues. Of the six cysteines, disulfide bonds typically are found between the following cysteines: C1 and C3, C2 and C5, C4 and C6. The A domain constitutes a ligand binding moiety. The cysteine residues of the domain are disulfide linked to form a compact, stable, functionally independent moiety. Clusters of these repeats make up a ligand binding domain, and differential clustering can impart specificity with respect to the ligand binding. Exemplary proteins containing A-domains include, e.g., complement components (e.g., C6, C7, C8, C9, and Factor I), serine proteases (e.g., enteropeptidase, matriptase, and corin), transmembrane proteins (e.g., ST7, LRP3, LRP5 and LRP6) and endocytic receptors (e.g., Sortilin-related receptor, LDL-receptor, VLDLR, LRP1, LRP2, and ApoER2). Methods for making A domain proteins of a desired binding specificity are disclosed, for example, in WO 02/088171 and WO 04/044011, each of which is incorporated herein by reference.

In other embodiments, a pharmaceutically active moiety of the invention comprises a binding site from a repeat protein. Repeat proteins are proteins that contain consecutive copies of small (e.g., about 20 to about 40 amino acid residues) structural units or repeats that stack together to form contiguous domains. Repeat proteins can be modified to suit a particular target binding site by adjusting the number of repeats in the protein. Exemplary repeat proteins include Designed Ankyrin Repeat Proteins (i.e., a DARPins®, Molecular Partners, Zurich, Switzerland) (see e.g., Binz et al., Nat. Biotechnol., 22: 575-582 (2004)) or leucine-rich repeat proteins (ie., LRRPs) (see e.g., Pancer et al., Nature, 430: 174-180 (2004)). All so far determined tertiary structures of ankyrin repeat units share a characteristic composed of a β-hairpin followed by two antiparallel α-helices and ending with a loop connecting the repeat unit with the next one. Domains built of ankyrin repeat units are formed by stacking the repeat units to an extended and curved structure. LRRP binding sites from part of the adaptive immune system of sea lampreys and other jawless fishes and resemble antibodies in that they are formed by recombination of a suite of leucine-rich repeat genes during lymphocyte maturation. Methods for making DARpin or LRRP binding sites are described in WO 02/20565 and WO 06/083275, each of which is incorporated herein by reference.

Other non-immunoglobulin binding sites which may be employed in binding molecules of the invention include binding sites derived from Src homology domains (e.g. SH2 or SH3 domains), PDZ domains, beta-lactamase, high affinity protease inhibitors, or small disulfide binding protein scaffolds such as scorpion toxins. Methods for making binding sites derived from these molecules have been disclosed in the art, see e.g., Silverman et al., Nat. Biotechnol., 23(12): 1493-4 (2005); Panni et al, J. Biol. Chem., 277: 21666-21674 (2002), Schneider et al., Nat. Biotechnol., 17: 170-175 (1999); Legendre et al., Protein Sci., 11:1506-1518 (2002); Stoop et al., Nat. Biotechnol., 21: 1063-1068 (2003); and Vita et al., PNAS, 92: 6404-6408 (1995). Yet other binding sites may be derived from a binding domain selected from the group consisting of an EGF-like domain, a Kringle-domain, a PAN domain, a Gla domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, a Laminin-type EGF-like domain, a C2 domain, a CTLA-4 domain, and other such domains known to those of ordinary skill in the art, as well as derivatives and/or variants thereof. Additional non-immunoglobulin polypeptides include Avimers®

(Avidia, Inc., Mountain View, Calif.—see International PCT Publication No. WO 06/055689 and US Patent Pub 2006/ 0234299), Telobodies® (Biotech Studio, Cambridge, Mass.), Evibodies® (Evogenix, Sydney, Australia—see U.S. Pat. No. 7,166,697), and Microbodies® (Nascacell Technologies, Munich, Germany).

iii. Binding Portions of Receptors or Ligands

In other aspects, a pharmaceutically active moiety of the invention is a ligand binding portion of a receptor and/or a receptor binding portion of a ligand.

In other exemplary embodiments, a pharmaceutically active moiety of the invention may comprise one or more ligand binding domains or receptor binding domains derived from one or more of the following proteins:

a. Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IL10 receptor, IFNγ (EP0240975), and the TNF family of receptors (e.g., TNFα (e.g. TNFR-1 (EP 417, 563), TNFR-2 (EP 417,014) lymphotoxin beta receptor).

b. Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a fusion protein of the invention. Leukocyte homing receptors are expressed on leukocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

c. Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

d. Hormones

Exemplary growth hormones for use as pharmacologically active moieties in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH); calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

e. Receptors and Ligands

In one embodiment, a pharmaceutically active moiety of the invention combines the binding site(s) of the ligand or receptor (e.g. the extracellular domain (ECD) of a receptor) with at least one genetically-fused Fc region (i.e., scFc region). In certain embodiments, the binding site or domain of the ligand-binding portion of a receptor may be derived from a receptor bound by an antibody or antibody variant. In other embodiments, the ligand binding portion of a receptor is derived from a receptor selected from the group consisting of a receptor of the Immunoglobulin (Ig) superfamily (e.g., a soluble T-cell receptor, e.g., mTCR® (Medigene AG, Munich, Germany), a receptor of the TNF receptor superfamily described supra (e.g., a soluble TNFα receptor of an immunoadhesin), a receptor of the Glial Cell-Derived Neurotrophic Factor (GDNF) receptor family (e.g., GFRα3), a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In other embodiments, the binding site or domain of the receptor-binding portion of a ligand may be derived from a ligand bound by an antibody or antibody variant. For example, the ligand may bind a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily. In one exemplary embodiment, the binding site of the receptor-binding portion of a ligand is derived from a ligand belonging to the TNF ligand superfamily (e.g., CD40L).

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), glial cell derived neurotrophic factor ligands (e.g., GDNF, neuturin, artemin, and persephin), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); Thrombopoeitin (TPO; stem-cell factor (SCF), thrombopoietin (TPO, c-Mpl ligand), and the Wnt polypeptides (U.S. Pat. No. 6,159,462).

Exemplary growth factor receptors which may be used as pharmacologically active moieties of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as p75$^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

f. Drugs

In another embodiment, a pharmacologically active agent is a drug substance used in the treatment, cure, prevention, or diagnosis of disease or used to otherwise enhance physical or mental well-being. Such drugs may be chemical entities and exemplary such entities are described in more detail herein.

The present invention may be applied to deliver other agents for the treatment of disorders affecting the nervous system and it may also be applied for diagnostic purposes. Preferred classes of agents for treatment of CNS disorders include:

Drugs acting at synaptic and neuroeffector junctional sites; general and local analgesics and anesthetics such as opioid analgesics and antagonists; hypnotics and sedatives; drugs for the treatment of psychiatric disorders such as depression, schizophrenia; anti-epileptics and anticonvulsants; Huntington's disease, aging and Alzheimer's disease; neuroprotective agents (such as excitatory amino acid antagonists and neurotropic factors) and neuroregenerative agents; trophic factors such as brain derived neurotrophic factor, ciliary neurotrophic factor, or nerve growth factor; drugs aimed at the treatment of CNS trauma or stroke; and drugs for the treatment of addiction and drug abuse; autacoids and anti-inflammatory drugs; chemotherapeutic agents for parasitic infections and microbial diseases; immunosuppressive agents and anti-cancer drugs; hormones and hormone antagonists; heavy metals and heavy metal antagonists; antagonists for non-metallic toxic agents; cytostatic agents for the treatment of cancer; diagnostic substances for use in nuclear medicine, and radiation therapy immunoactive and immunoreactive agents; and a number of other agents such as transmitters and their respective receptor-agonists and -antagonists, their respective precursors or metabolites; antibiotics, antispasmodics, antihistamines, antinauseants, relaxants, stimulants, "sense" and "anti-sense" oligonucleotides, cerebral dilators, psychotropics, anti-manics, vascular dilators and constrictors, anti-hypertensives, migraine treatments, hypnotics, hyper- or hypo-glycemic agents, mineral or nutritional agents, anti-obesity drugs, anabolics and anti-asthmatics.

Typical active ingredients (e.g., drugs) can be any substance affecting the nervous system or used for diagnostic tests of the nervous system. These are described by Gilman et al. (1990), "Goodman and Gilman's—The Pharmacological Basis of Therapeutics", Pergamon Press, New York, and include the following agents:

acetylcholine and synthetic choline esters, naturally occurring cholinomimetic alkaloids and their synthetic congeners, anticholinesterase agents, ganglionic stimulants, atropine, scopolamine and related antimuscarinic drugs, catecholamines and sympathomimetic drugs, such as epinephrine, norepinephrine and dopamine, adrenergic agonists, adrenergic receptor antagonists, transmitters such as GABA, glycine, glutamate, acetylcholine, dopamine, 5-hydroxytryptamine, and histamine, neuroactive peptides;

analgesics and anesthetics such as opioid analgesics and antagonists; preanesthetic and anesthetic medications such as benzodiazepines, barbiturates, antihistamines, phenothiazines and butylphenones; opioids; antiemetics; anticholinergic drugs such as atropine, scopolamine or glycopyrrolate; cocaine; chloral derivatives; ethchlorvynol; glutethimide; methyprylon; meprobamate; paraldehyde; disulfiram; morphine, fentanyl and naloxone;

centrally active antitussive agents;

psychiatric drugs such as phenothiazines, thioxanthenes and other heterocyclic compounds (e.g., halperiodol); tricyclic antidepressants such as desimipramine and imipramine; atypical antidepressants (e.g., fluoxetine and trazodone), monoamine oxidase inhibitors such as isocarboxazid; lithium salts; anxiolytics such as chlordiazepoxyd and diazepam;

anti-epileptics including hydantoins, anticonvulsant barbiturates, iminostilbines (such as carbamazepine), succinimides, valproic acid, oxazolidinediones and benzodiazepines.

anti-Parkinson drugs such as L-DOPA/CARBIDOPA, apomorphine, amantadine, ergolines, selegeline, ropinorole, bromocriptine mesylate and anticholinergic agents;

antispasticity agents such as baclofen, diazepam and dantrolene;

neuroprotective agents, such as excitatory amino acid antagonists, neurotrophic factors and brain derived neurotrophic factor, ciliary neurotrophic factor, or nerve growth factor; neurotrophin(NT) 3 (NT3); NT4 and NT5; gangliosides; neuroregenerative agents;

drugs for the treatment of addiction and drug abuse include opioid antagonists and anti-depressants;

autocoids and anti-inflammatory drugs such as histamine, bradykinin, kallidin and their respective agonists and antagonists;

chemotherapeutic agents for parasitic infections and microbial diseases;

anti-cancer drugs including alkylating agents (e.g., nitrosoureas) and antimetabolites; nitrogen mustards, ethylenamines and methylmelamines; alkylsulfonates; folic acid analogs; pyrimidine analogs, purine analogs, vinca alkaloids; and antibiotics.

The present invention is also useful for the delivery of anti-nauseants, relaxants, stimulants, "sense" and "anti-sense" oligonucleotides, cerebral dilators, psychotropics, vascular dilators and constrictors, anti-hypertensives, migraine treatments, hyper- or hypo-glycemic agents, mineral or nutritional agents, anti-obesity drugs, anabolics and anti-asthmatics, anti-inflammatory drugs such as phenylbutazone, indomethacin, naproxen, ibuprofen, flurbiprofen, diclofenac, dexamethasone, prednisone and prednisolone; cerebral vasodilators such as soloctidilum, vincamine, naftidrofuryl oxalate, co-dergocrine mesylate, cyclandelate, papaverine, nicotinic acid, anti-infective agents such as erythromycin stearate, and cephalexin.

adrenocorticotropic hormone, adenosine deaminase ribonuclease, alkaline phosphatase, angiotensin, antibodies, arginase, arginine deaminease, asparaginase, caerulein, calcitonin, chemotrypsin, cholecystokinin, clotting factors, dynorphins, endorphins, endorphins, enkephalins, enkephalins, erythropoietin, gastrin-releasing peptide, glucagon, hemoglobin, hypothalmic releasing factors, interferon, katacalcin, motilin, neuropeptide Y, neurotensin, non-naturally occurring opioids, oxytosin, papain, parathyroid hormone, peptides prolactin, soluble CD-4, somatomedin, somatostatin, somatostatin, somatotropin, superoxide dismutase, thyroid stimulating hormone, tissue plasminogen activator, trypsin, vasopressin, and analogues of such peptides, as well as other suitable enzymes, hormones, proteins, polypeptides, enzyme-protein conjugates, antibody-hapten conjugates, viral epitopes, etc.

V. Exemplary Formats of Polypeptides

Exemplary formats of binding molecules of the invention are set forth in the accompanying Figures. For example FIG. 1 includes embodiments in which the pharmaceutically active moiety is not illustrated (e.g., FC5Fc and FcFC5 scaffolds to which pharmaceutically active moieties can be added) as well as embodiments in which the pharmaceutically active moiety is an antibody binding site. For example, in one embodiment, a scaffold of a binding molecule of the invention (i.e., a construct to which a pharmaceutically active moiety can be added) comprises two BBB transmigrating moieties covalently linked (e.g., genetically fused) to an Fc region, domain, or moiety. The BBB transmigrating moieties may be linked directly or via a linker peptide. In a preferred embodiment, the BBB transmigrating moieties may be linked to the N terminus of the Fc region, domain, or moiety. In one embodiment, additional binding moieties (e.g., non-TMEM30A pharmacologically active moieties in the form of scFv molecules) may also be linked to the C terminus of the Fc region, domain or moiety.

In another embodiment, additional BBB transmigrating moieties may be linked to the C terminus of the Fc region, domain, or moiety. The BBB transmigrating moieties may be linked directly or via a linker peptide.

In another embodiment, a binding molecule of the invention comprises a BBB transmigrating moiety N-terminally fused to the VH domain of an intact antibody molecule. In another embodiment, a binding molecule of the invention comprises BBB transmigrating moiety N terminally fused to the VL domain of an intact antibody molecule. In yet another embodiment, a binding molecule of the invention comprises two BBB transmigrating moiety C terminally fused to an intact antibody molecule. The BBB transmigrating moieties may be linked directly or via a linker peptide.

It will be understood that pharmaceutically active moieties (or additional pharmacologically active moieties) may be attached to any of these constructs using methods known in the art.

In one embodiment, the polypeptides of the invention comprise only one pharmaceutically active moiety (creating a molecule which is monomeric with regard to the pharmaceutically active moiety, but which is multimeric (e.g., dimeric) with regard to BBB transmigrating moieties). In another embodiment, a polypeptide of the invention comprises more than one pharmacologically active moiety, e.g., 2, 3, 4, 5, 6, 7, 8, 9, 10, or more pharmacologically active moieties. The pharmaceutically active moieties may be the same or different.

In one embodiment of the invention, a pharmaceutically active moiety is operably linked via a linker peptide to the N-terminus of an Fc domain, region, or moiety. In another embodiment, the pharmacologically active moiety is operably linked via a linker peptide to the C-terminus of an Fc domain, region, or moiety.

In other embodiments, two or more pharmaceutically active moieties are linked to each other (e.g., via a linker peptide) in series. In one embodiment, the tandem array of pharmaceutically active moieties is operably linked via a linker peptide to either the C-terminus or the N-terminus of an Fc region, domain, or moiety.

Other methods of conjugating, linking and coupling proteins to pharmacologically active compounds are well known in the field. For example, see Wu A M, Senter P D, Arming antibodies: prospects and challenges for immuno-conjugates, Nat. Biotechnol. 2005 September; 23(9):1137-46 and Trail P A, King H D, Dubowchik G M, Monoclonal antibody drug immunoconjugates for targeted treatment of cancer, Cancer Immunol Immunother. 2003 May; 52(5): 328-37; Saito G, Swanson J A, Lee K D. Drug delivery strategy utilizing conjugation via reversible disulfide linkages: role and site of cellular reducing activities, Adv Drug Deliv Rev. 2003 Feb. 10; 55(2):199-215. As well, the present antibodies may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000 and Martin et al., Nanomaterials in Analytical Chemistry, Analytical Chemistry News & Features, May 1, 1998; pp. 322 A-327 A).

Many effector molecules lack suitable functional groups to which binding polypeptides can be linked. In one embodiment, an effector molecule, e.g., a drug or prodrug is attached to the polypeptide through a linking molecule. In one embodiment, the linking molecule contains a chemical bond that allows for the activation of cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking molecule comprises a disulfide bond or a thioether bond. In accordance with the invention, the linking molecule preferably comprises a reactive chemical group. Particularly preferred reactive chemical groups are N-succinimidyl esters and N-sulfosuccinimidyl esters. In a preferred embodiment, the reactive chemical group can be covalently bound to the effector via disulfide bonding between thiol groups. In one embodiment an effector molecule is modified to comprise a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

In one embodiment, a linking molecule may be used to join an effector molecule with a polypeptide of the invention. The linking molecule may be cleavable or non-cleavable. In one embodiment, the cleavable linking molecule is a redox-cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides. The cleaving stimulus can be provided upon intracellular uptake of the binding protein of the invention where the lower redox potential of the cytoplasm facilitates cleavage of the linking molecule. In another embodiment, a decrease in pH triggers the release of the maytansinoid cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linking molecules which may be used to target lysosomes or endosomes of cancer cells, include those with acid-cleavable bonds such as those found in acetals, ketals, orthoesters, hydrazones, trityls, cis-aconityls, or thiocarbamoyls (see for example, Willner et al., (1993), *Bioconj. Chem.*, 4: 521-7;

U.S. Pat. Nos. 4,569,789, 4,631,190, 5,306,809, and 5,665,358). Other exemplary acid-sensitive linking molecules comprise dipeptide sequences Phe-Lys and Val-Lys (King et al., (2002), *J. Med. Chem.,* 45: 4336-43). The cleaving stimulus can be provided upon intracellular uptake trafficking to low pH endosomal compartments (e.g. lysosomes). Other exemplary acid-cleavable linking molecules are the molecules that contain two or more acid cleavable bonds for attachment of two or more maytansinoids (King et al., (1999), *Bioconj. Chem.,* 10: 279-88; WO 98/19705).

Cleavable linking molecules may be sensitive to biologically supplied cleaving agents that are associated with a particular target cell, for example, lysosomal or tumor-associated enzymes. Examples of linking molecules that can be cleaved enzymatically include, but are not limited to, peptides and esters. Exemplary enzyme cleavable linking molecules include those that are sensitive to tumor-associated proteases such as Cathepsin B or plasmin (Dubowchik et al., (1999), *Pharm. Ther.,* 83: 67-123; Dubowchik et al., (1998), *Bioorg. Med. Chem. Lett.,* 8: 3341-52; de Groot et al., (2000), *J. Med. Chem.,* 43: 3093-102; de Groot et al., (1999)m 42: 5277-83). Cathepsin B-cleavable sites include the dipeptide sequences valine-citrulline and phenylalanine-lysine (Doronina et al., (2003), *Nat. Biotech.,* 21(7): 778-84); Dubowchik et al., (2002), *Bioconjug. Chem.,* 13: 855-69). Other exemplary enzyme-cleavable sites include those formed by oligopeptide sequences of 4 to 16 amino acids (e.g., Suc-β-Ala-Leu-Ala-Leu (SEQ ID NO: 11)) which recognized by trouse proteases such as Thimet Oliogopeptidase (TOP), an enzyme that is preferentially released by neutrophils, macrophages, and other granulocytes.

In certain particular aspects, a binding polypeptide of the invention is multispecific, e.g., has at least one binding site that binds to a first molecule or epitope of a molecule and at least one second binding site that binds to a second molecule or to a second epitope of the first molecule. Multispecific binding molecules of the invention may comprise at least two binding sites. In certain embodiments, at least two binding site of a multispecific binding molecule of the invention are BBB transmigrating sites.

VI. Synthesis of Binding Molecules

Having selected the format of a polypeptide of the invention, a variety of methods are available for producing the polypeptide. Such methods include, but are not limited to chemical synthesis techniques and recombinant DNA expression techniques.

In one embodiment, the invention pertains to a nucleic acid construct comprising a nucleic acid sequence encoding a polypeptide molecule of the invention. It will be understood that because of the degeneracy of the code, a variety of nucleic acid sequences will encode the amino acid sequence of the polypeptide. The desired polynucleotide can be produced using methods known in the art (e.g., by de novo solid-phase DNA synthesis or by PCR mutagenesis of an earlier prepared polynucleotide encoding the target polypeptide).

Oligonucleotide-mediated mutagenesis is one method for preparing a substitution, in-frame insertion, or alteration (e.g., altered codon) to introduce a codon encoding an amino acid substitution (e.g., into an Fc variant moiety). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a polypeptide of the invention.

For recombinant production, a polynucleotide sequence encoding the polypeptide is inserted into an appropriate expression vehicle, i. e., a vector which contains the necessary elements for the transcription and translation of the inserted coding sequence, or in the case of an RNA viral vector, the necessary elements for replication and translation.

The nucleic acid encoding the polypeptide is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14: 725) and electroporation (Neumann et al. 1982, EMBO, J. 1: 841). A variety of host-expression vector systems may be utilized to express the polypeptide described herein in eukaryotic cells. In one embodiment, the eukaryotic cell is an animal cell, including mammalian cells (e. g. CHO, BHK, Cos, HeLa cells). When the polypeptide is expressed in a eukaryotic cell the DNA encoding the polypeptide may also code for a signal sequence that will permit the polypeptide to be secreted. One skilled in the art will understand that while the protein is translated the signal sequence is cleaved by the cell to form the mature polypeptide. In one embodiment, the invention pertains to mature polypeptides comprising a linker peptide of the invention. Alternatively, where a signal sequence is not included the polypeptide can be recovered by lysing the cells.

The polypeptide of the invention can also be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82: 4438). Methods of producing transgenic animals are known in the art, including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

Expression vectors can encode for tags that permit for easy purification or identification of the recombinantly produced polypeptide. Examples include, but are not limited to, vector pUR278 (Ruther et al. 1983, EMBO J. 2: 1791) in which the polypeptide described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e. g. PreCission Protease (Pharmacia, Peapack, N.J.)) for easy removal of the tag after purification.

For the purposes of this invention, numerous different art recognized expression vector systems may be employed.

These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

In other preferred embodiments the polypeptides of the instant invention may be expressed using polycistronic constructs. In these expression systems, multiple gene products of interest such as multiple polypeptides of multimer binding protein may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a polypeptide has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan. Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian large scale cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag (SEQ ID NO: 12)) may optionally be attached or included within the polypeptide sequence to facilitate downstream purification.

One skilled in the art can easily synthesize smaller peptides for use in connection with the invention. Standard procedures for preparing synthetic peptides are well known in the art. The peptides can be synthesized using the solid phase peptide synthesis (SPPS) method of Merrifield (J. Am. Chem. Soc., 85:2149 (1964), which is incorporated herein by reference) or using standard solution methods well known in the art (see, for example, Bodanzsky, M., Principles of Peptide Synthesis 2nd revised ed. (Springer-Verlag, 1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431 A-01 Peptide Synthesizer (Mountain View, Calif.) or using the manual peptide synthesis technique described by Houghten, Proc. Nat. Acad. Sci., USA 82:5131 (1985), which is incorporated herein by reference.

Peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamidomethyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, J. Org. Chem. 47:3258 (1982), which is incorporated herein by reference.

VII. Purification of Binding Molecules

Once expressed, polypeptides of the invention can be purified according to standard procedures in the art, including, e.g., ammonium sulfate precipitation, affinity column chromatography, HPLC purification, gel electrophoresis and the like (see generally Scopes, Protein Purification (Springer-Verlag, N.Y., (1982)). A newly synthesized peptide can also be purified using a method such as reverse phase high performance liquid chromatography (RP-HPLC) or other methods of separation based on the size or charge of the peptide. Furthermore, the purified peptide can be characterized using these and other well known methods such as amino acid analysis and mass spectrometry.

Substantially pure proteins of at least about 90 to 95% homogeneity are preferred, and 98 to 99% or more homogeneity most preferred, for pharmaceutical uses.

VIII. Methods of Administration

Methods of preparing and administering polypeptides of the invention to a subject are well known to or are readily determined by those skilled in the art.

Compositions for administration to a subject include nucleic acid molecules which comprise a nucleotide sequence encoding a binding molecule of the invention (for gene therapy applications) as well as polypeptide molecules.

Methods of introduction include but are not limited to intradermal, intramuscular, intraperitoneal, intravenous, subcutaneous, intranasal, epidural, and oral routes. The conjugates may be administered by any convenient route, for example by infusion or bolus injection, by absorption through epithelial or mucocutaneous linings (e.g., oral mucosa, rectal and intestinal mucosa, etc.) and may be administered together with other pharmacologically active agents. Administration can be systemic or local.

In certain circumstances, it may be desirable to introduce the pharmaceutical compositions of the invention directly into the central nervous system by any suitable route, including intraventricular and intrathecal injection; intraventricular injection may be facilitated by an intraventricular catheter, for example, attached to a reservoir, such as an Ommaya reservoir.

Pulmonary or nasal administration can also be employed, e.g., by use of an inhaler or nebulizer, and formulation with an aerosolizing agent.

In another embodiment, the conjugates can be delivered in a controlled release system. In one embodiment, a pump may be used (see Langer, supra; Sefton, CRC Crit. Ref. Biomed. Eng. 14:201 (1987); Buchwald et al., Surgety 88:507 (1980); Saudek et al., N. Engl. J. Med. 321:574 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

The subject is preferably an animal, including, but not limited to, animals such as cows, pigs, horses, chickens, cats, dogs, etc., and is preferably a mammal, and most preferably human.

Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit which will preferably have labels or package inserts indicating that the associated compositions are useful for treating a subject suffering from, or predisposed to autoimmune or neoplastic disorders.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated.

Treatment dosages may be titrated using routine methods known to those of skill in the art to optimize safety and efficacy. In one embodiment, a polypeptide of the invention is one that has been previously administered to patients, but which has been modified to comprise a linker peptide of the invention in place of a traditional linker peptide. In such cases, the dosage of polypeptide administered will be consistent with that previously found to be safe and effective, i.e., the standard of care.

Polypeptides of the invention can be administered on multiple occasions. Intervals between single dosages can be weekly, monthly or yearly. Intervals can also be irregular as indicated by measuring blood levels of polypeptide, polypeptide target, or antigen in the patient. In some methods, dosage is adjusted to achieve a particular in vivo concentration. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance. Such an amount is defined to be a "prophylactic effective dose." A relatively low dosage may be administered at relatively infrequent intervals over a long period of time. Some patients continue to receive treatment for the rest of their lives.

In therapeutic applications, a relatively high dosage at relatively short intervals may be administered sometimes required until progression of the disease is reduced or terminated, and preferably until the patient shows partial or complete amelioration of symptoms of disease.

It will further be appreciated that the molecules of the instant invention may be used in conjunction or combination with an agent or agents (e.g. to provide a combined therapeutic regimen). Exemplary agents with which a molecule of the invention may be combined include agents that represent the current standard of care for a particular disorder being treated. Such agents may be chemical or biologic in nature. The term "biologic" or "biologic agent" refers to any pharmaceutically active agent made from living organisms and/or their products which is intended for use as a therapeutic.

Polypeptides of the invention can optionally be administered in combination with other agents that are effective in treating the disorder or condition in need of treatment (e.g., prophylactic or therapeutic). As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. For example, chemotherapeutic or biologic agents could be administered in standard, well known courses of treatment in conjunction with the subject binding molecules. A skilled artisan (e.g. a physician) would be readily be able to discern effective combined therapeutic regimens without undue experimentation based on the selected adjunct therapy and the teachings of the instant specification.

In one embodiment, a polypeptide can be produced in a patient by administration as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

The amount of agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9*th* ed. 1996). In another embodiment, an amount of such an agent consistent with the standard of care is administered.

As previously discussed, the polypeptides of the present invention, may be administered in a pharmaceutically effective amount for the in vivo treatment of mammalian disorders. In this regard, it will be appreciated that the molecule of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a polypeptide of the invention, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the molecule of the invention may be administered to a human or other animal in accordance with the aforementioned methods of treatment in an amount sufficient to produce a therapeutic or prophylactic effect.

The mode of administration and dosage forms will of course affect the therapeutic amounts of the compounds which are desirable and efficacious for the given treatment application. A therapeutically effective amount is an amount necessary to prevent, delay or reduce the severity of the onset of disease, or an amount necessary to arrest or reduce the severity of an ongoing disease. It will be readily apparent to one of skill in the art that this amount will vary based on factors such as the weight and health of the recipient, the type of cells being transformed, the mode of administration of the present compositions and the type of medical disorder being treated.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

This invention is further illustrated by the following examples which should not be construed as limiting. The contents of all references, patents and published patent applications cited throughout this application are incorporated herein by reference.

Examples

Expression, Purification and Characterization of FC5 Molecules

Figure 2:
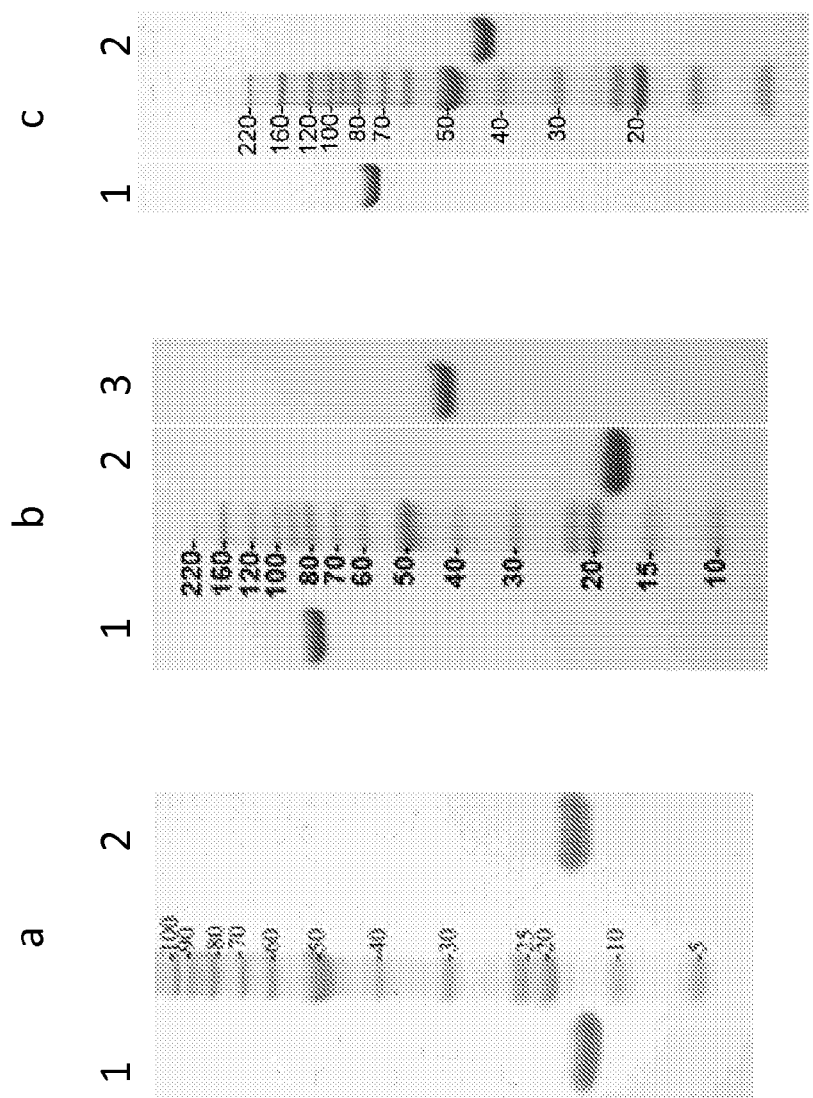
FIG. 2. The electrophoresis of 2.5 ug of each purified protein on a 4-12% Bis-Tris SDS PAGE is shown. SDS PAGE molecular weight standards from 10-220 kD are labeled on each gel. Shown in Panel A is nonreducing (1) and reducing lane (2) FC5, Panel B is nonreducing (1) and reducing lane (2) FC5-Fc, and Panel C is nonreducing (1) and reducing lane (2) Fc-FC5.

FC5 was expressed in *E. coli* and was purified using osmotic shock to release the soluble protein from the periplasmic space. The soluble His tagged FC5 was then captured from the lysate on a nickel column, by cation exchange on fractogel SE, followed by gel filtration on superdex 200. The camelid Vhh was characterized by SDS PAGE (FIG. 2*a-c*). FC5-Fc, Fc-FC5 and FC5-scram-Fc were expressed in DG44 CHO cell lines according to previously described methods. The desired hFc containing proteins were purified from the CHO cell fermentation medium (1 L) by adjusting the pH to 7.0 and capturing the protein on a 5 ml HiTrap rProteinA FF column (GE heathcare) that was previously equilibrated. All purified proteins were characterized for levels of endotoxin prior to injection to insure no generalized endotoxin dependent BBB opening would occur. Results are shown in Table I. Neuroactive peptides, Dalargin, Galanin or NPY were linked to the desired molecule (FC5, FC5-Fc) using succininmidyal-4-(N-maleimidomethyl)cyclohexane-1-carboxylate (SMCC) a bifunctional chemical linker using the methods described in Uto et al. 1991 (Uto, I., Ishimatsu, T., Hirayama, H., Ueda, S., Tsuruta, J., and Kambara, T. (1991) *Journal of immunological methods* 138(1), 87-94). Each peptide to be linked was synthesized with a cysteamide analog on the C-terminus this allowed for C-terminal crosslinking of the peptide via the free cysteine to the lysine side chains on the protein using the SMCC bifunctional crosslinking chemistry. Following crosslinking, each labeled molecule was purified by S-200 preparative gel filtration to eliminate any aggregates formed during the crosslinking reaction. The average number of peptides Dalargin, NPY or Galanin linked to each FC5 domain or FC5-Fc domains were determined by mass spectrometry. Table I shows average number of peptides linked per FC5, FC5-Fc or Fc-FC5 domain.

Circulating Pharmacokinetics of FC5 Containing Molecules:

To understand the exposure of the BBB endothelium to each of the FC5 containing antibodies the pharmacokinetics the molecules were determined in rats. Animals were dosed intraperitoneally at 3 mpk with either the FC5 Vhh N-terminally (FC5-Fc) or C-terminally (Fc-FC5) fused to a human Fc domain. Concentrations of FC5-Fc or Fc-FC5 in the plasma were determined at various time points by ELISA. The results were analyzed to determine the beta-phase half-lives of each construct (Table II). Results demonstrated the half-life of FC5-Fc and Fc-FC5 are significantly longer when fused to a human Fc than for the FC5 Vhh alone as the Fc is well known to impart recycling and the larger mass would prevent kidney filtration (Holt, L. J., Herring, C., Jespers, L. S., Woolven, B. P., and Tomlinson, I. M. (2003) *Trends in biotechnology* 21(11), 484-490).

Figure 3:
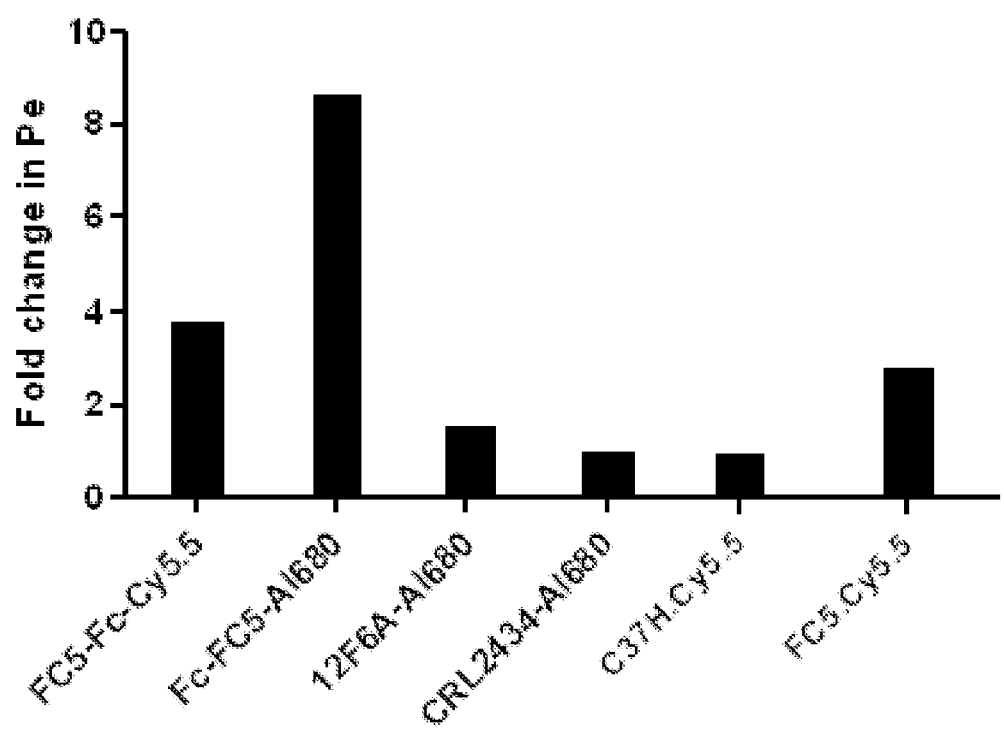
FIG. 3. Shows the increased rate of transport of FC5Fc, FcFC5 and FC5 across an in vitro SV40 rat BBB transformed endothelial cell line compared with control antibodies 12F6A (hIgG1), CRL2434 (mIgG1) and C37H ($V_{HH}$ only).

In Vitro Transport Rate of FC5 Containing Molecules:

We used an in vitro BBB endothelial cell layer to model in vivo cross BBB flux rates for each FC5 containing protein. The in vitro model uses a monolayer of immortalized adult rat brain endothelial cells (SV-ARBEC) in a monolayer assay system validated for tightness with small molecules (Garberg, P., Ball, M., Borg, N., Cecchelli, R., Fenart, L., Hurst, R. D., Lindmark, T., Mabondzo, A., Nilsson, J. E., Raub, T. J., Stanimirovic, D., Terasaki, T., Oberg, J. O., and Osterberg, T. (2005) *Toxicol In Vitro* 19(3), 299-334). The methods for the in vitro flux rate determinations are nearly identical to those described in (Caram-Salas, N., Boileau, E., Farrington, G. K., Garber, E., Brunette, E., Abulrob, A., and Stanimirovic, D. *Methods in molecular biology* 763, ed. 2010, 383-401). The influx rates were determined for FC5, FC5-Fc and Fc-FC5 across SV-ARBEC cell layer and the results are as shown in FIG. 3.

Figure 4A:
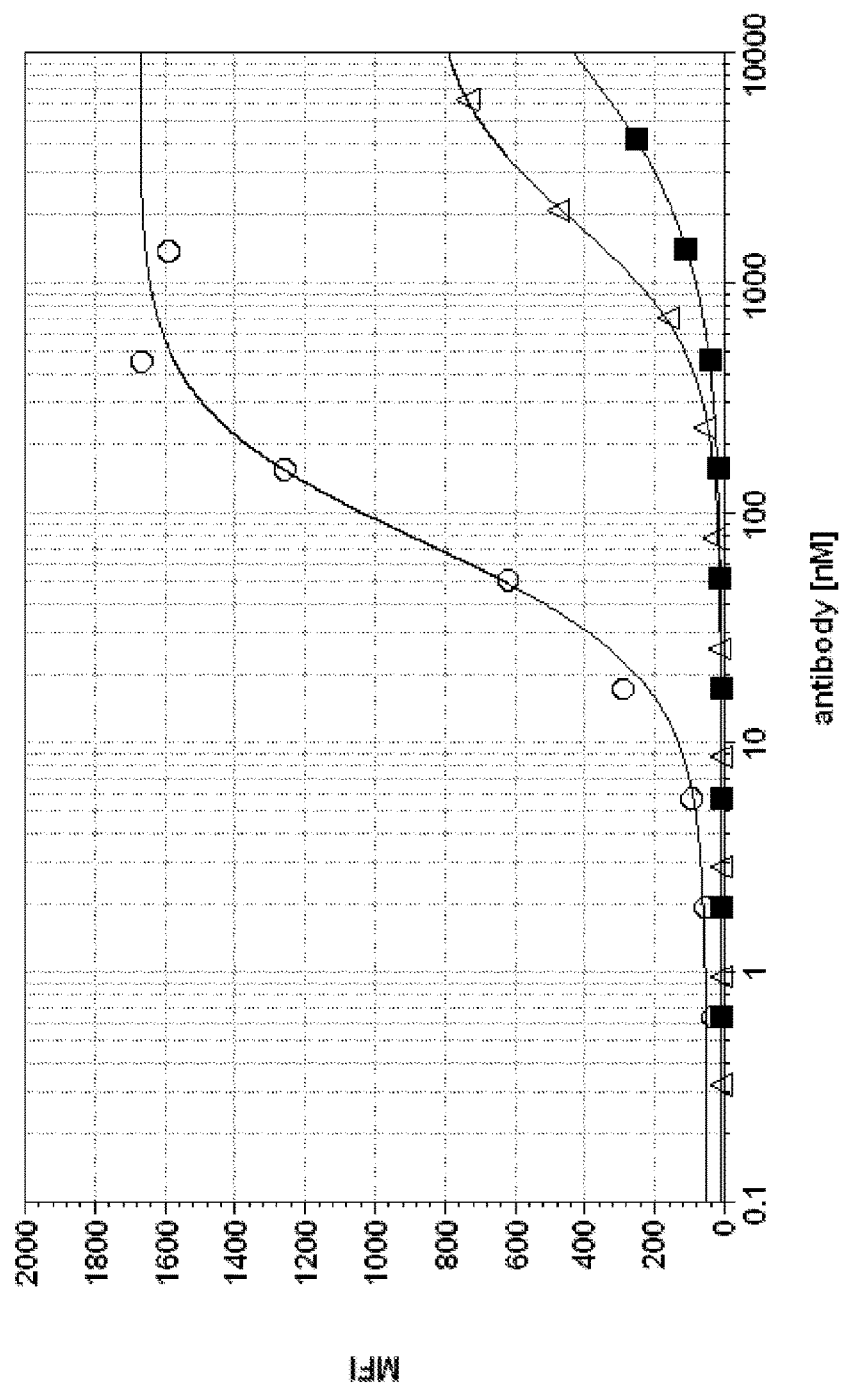
FIG. 4a-c. Panel 4(a) shows the binding of FC5-Fc (○), Fc-FC5 (■) or an irrelevant control camelid $V_{HH}$ fused to the N-termini of a huFc agly domain ($V_{HH}$-Fc) (Δ) to a SV40 rat BBB transformed endothelial cell line. Panel (4b) shows the binding of FC5-Fc (○) and Fc-FC5 (■) to a primary rat BBB endothelial cell line. Panel 4c shows the binding of FC5-Fc to rat (□) or human (◇) and Fc-FC5 to rat (▲) or human (•) TMEM30A transiently expressed in EBNA293 cells.
Figure 4B:
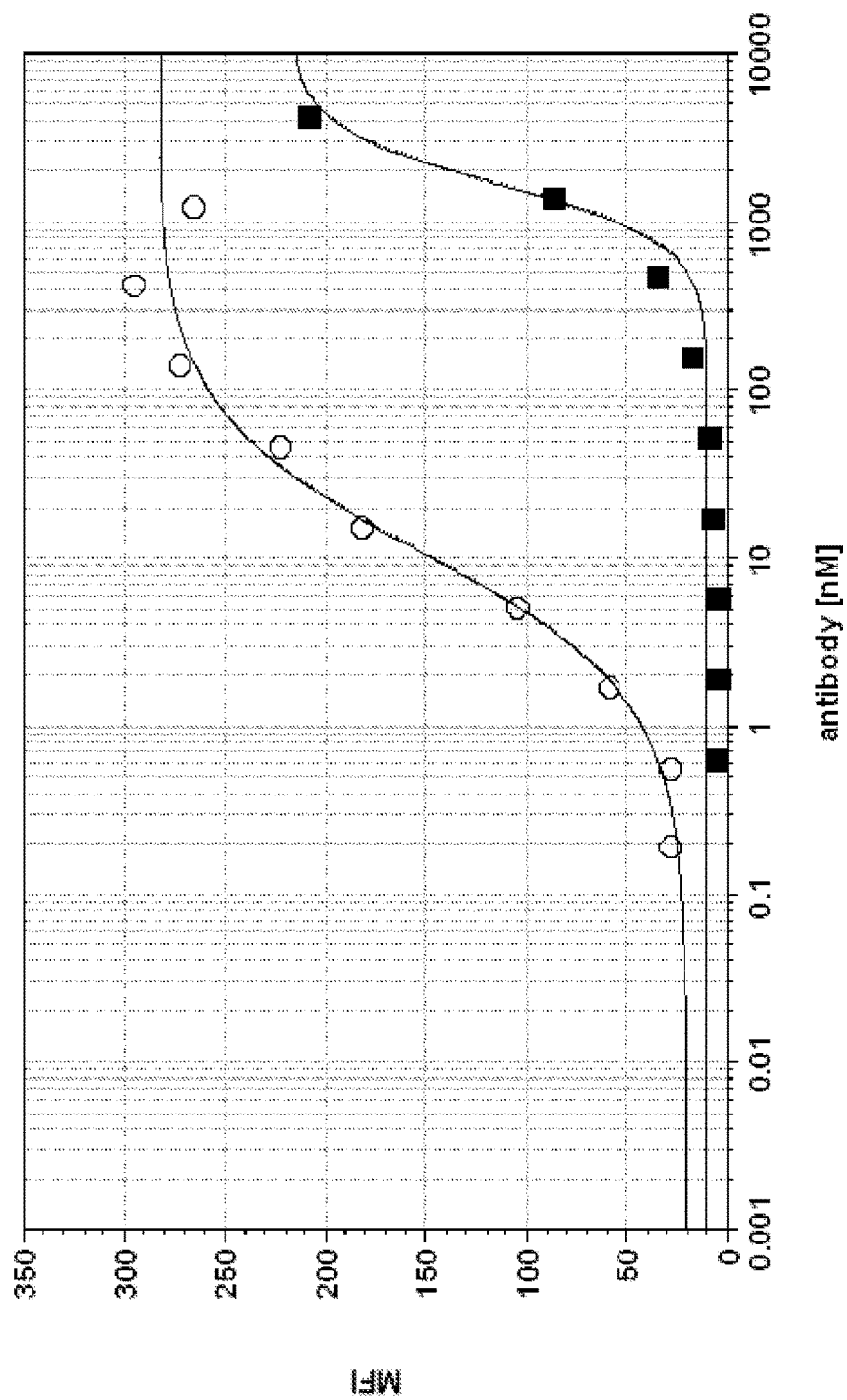
Figure 4C:
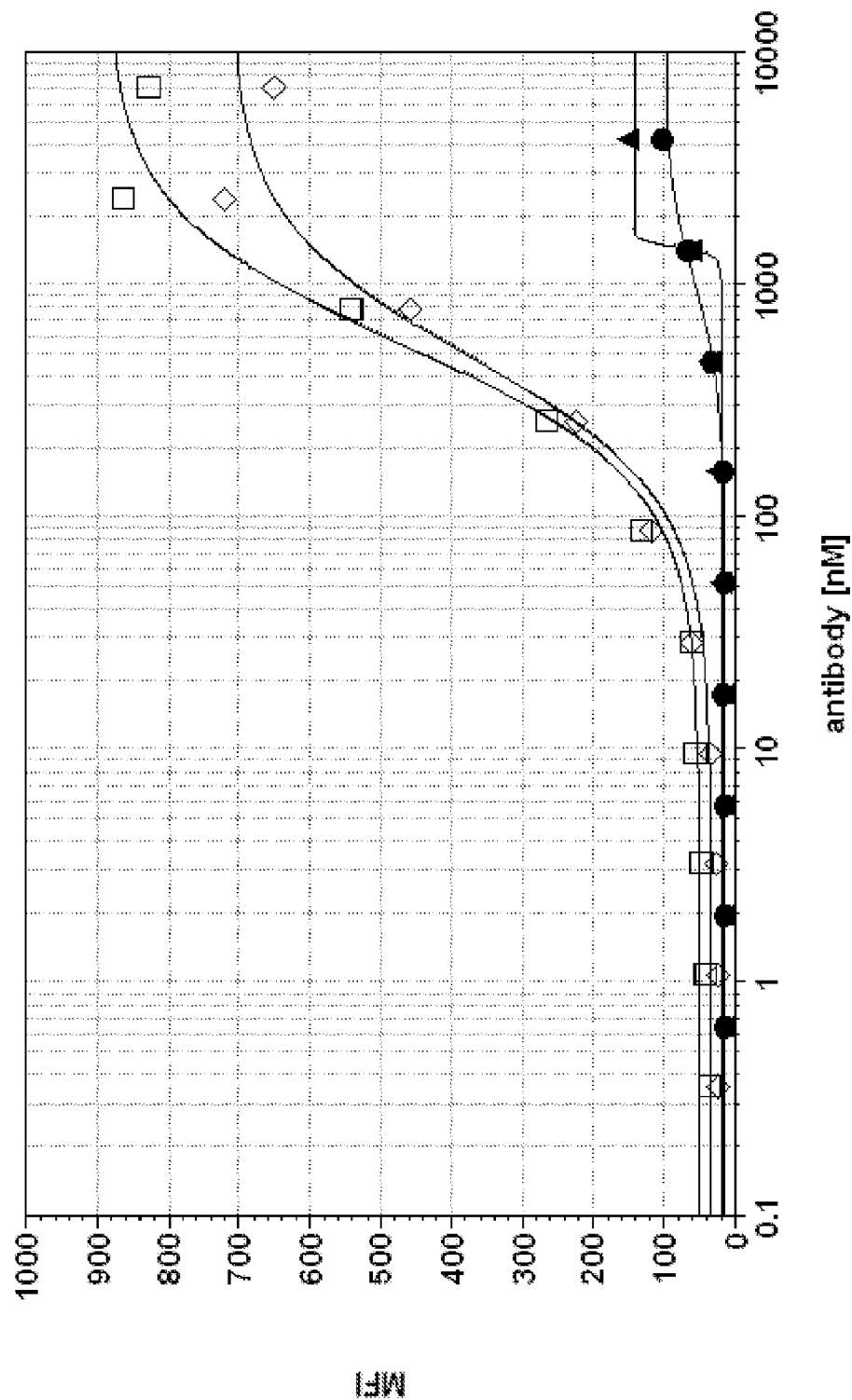
Figure 5:
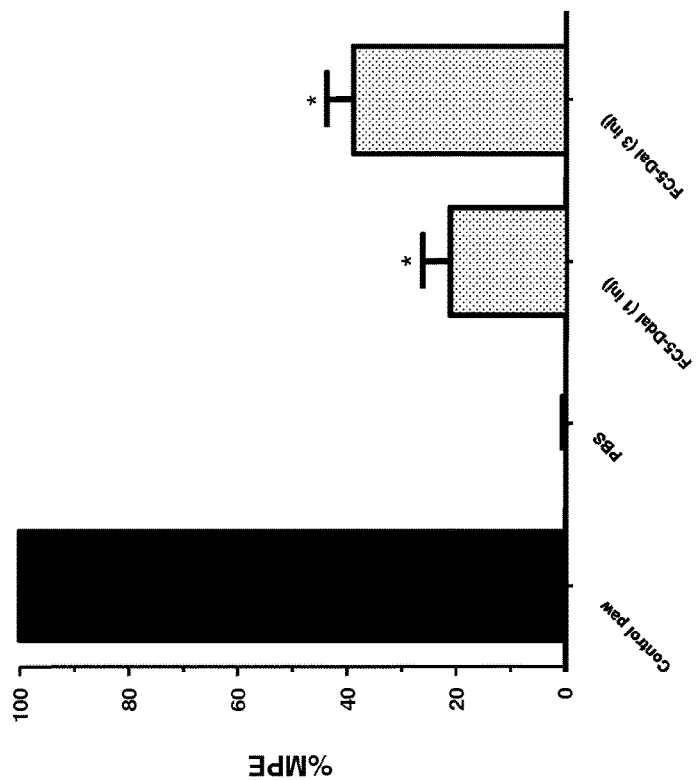
FIG. 5a-c. Panel 5a shows the ability of FC5 covalently cross-linked to Dalargin (FC5-Dal), to suppress pain in the Hargreaves animal model. The paw withdrawl rate is expressed as percent of maximum possible effect (% MPE) based on a 20 second time frame. The negative control shows the paw withdrawal rate for the contralateral non-inflamed control paw (•) and the positive control shows the rapid paw withdrawal rate of the inflamed paw when the rat is injected IV with PBS alone (○). The efficacy of a single IV dose (■) of FC5-Dal at 21 mg/Kg (mpk) is compared with three IV doses of FC5-Dal at 7 mpk (□) to suppress paw withdrawal rate in the Hargreaves animal. Panel 5b shows the average area under the curve for % MPE response versus time for each evaluated paw. Panel 5c shows additional negative control experiments in which rats are injected IV with three doses at time 0, 1 h and 2 h with either 7 mpk of either an irrelevant $V_{HH}$-Dal (gray boxes) or FC5 alone (open boxes). The contralateral control paw is also shown (closed circles). The % MPE for the suppression of paw withdrawal rate was determined in the Hargreaves animal.
Figure 5:
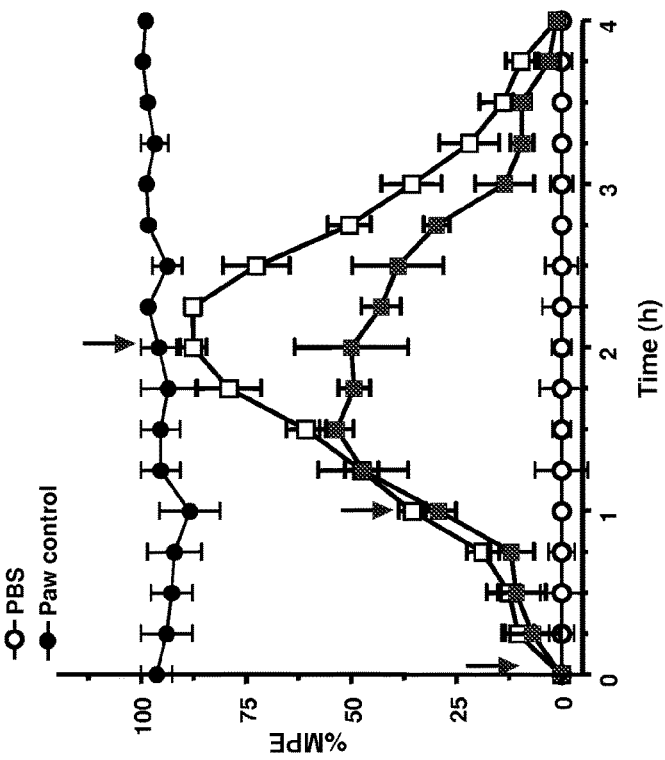
Figure 5C:
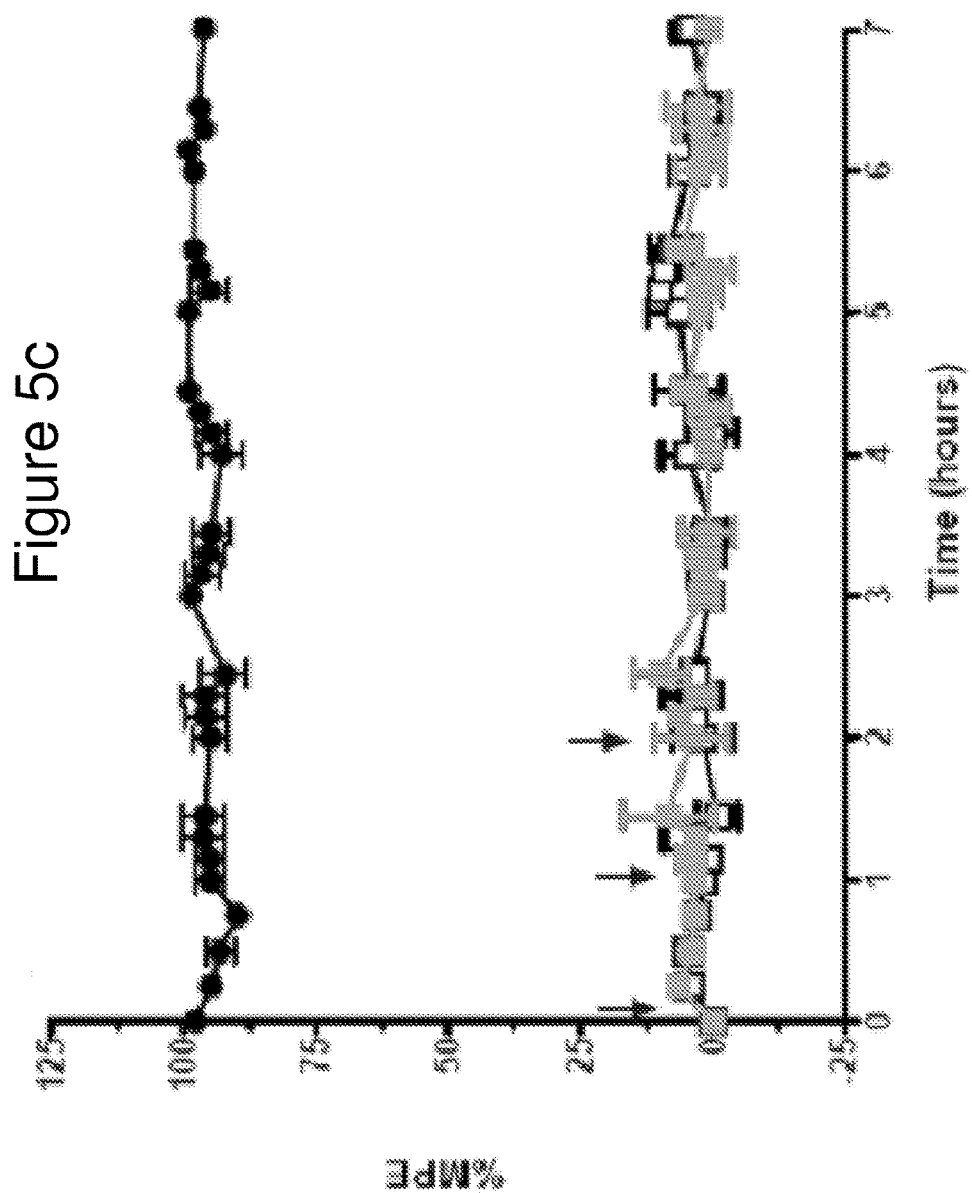
Figure 6:
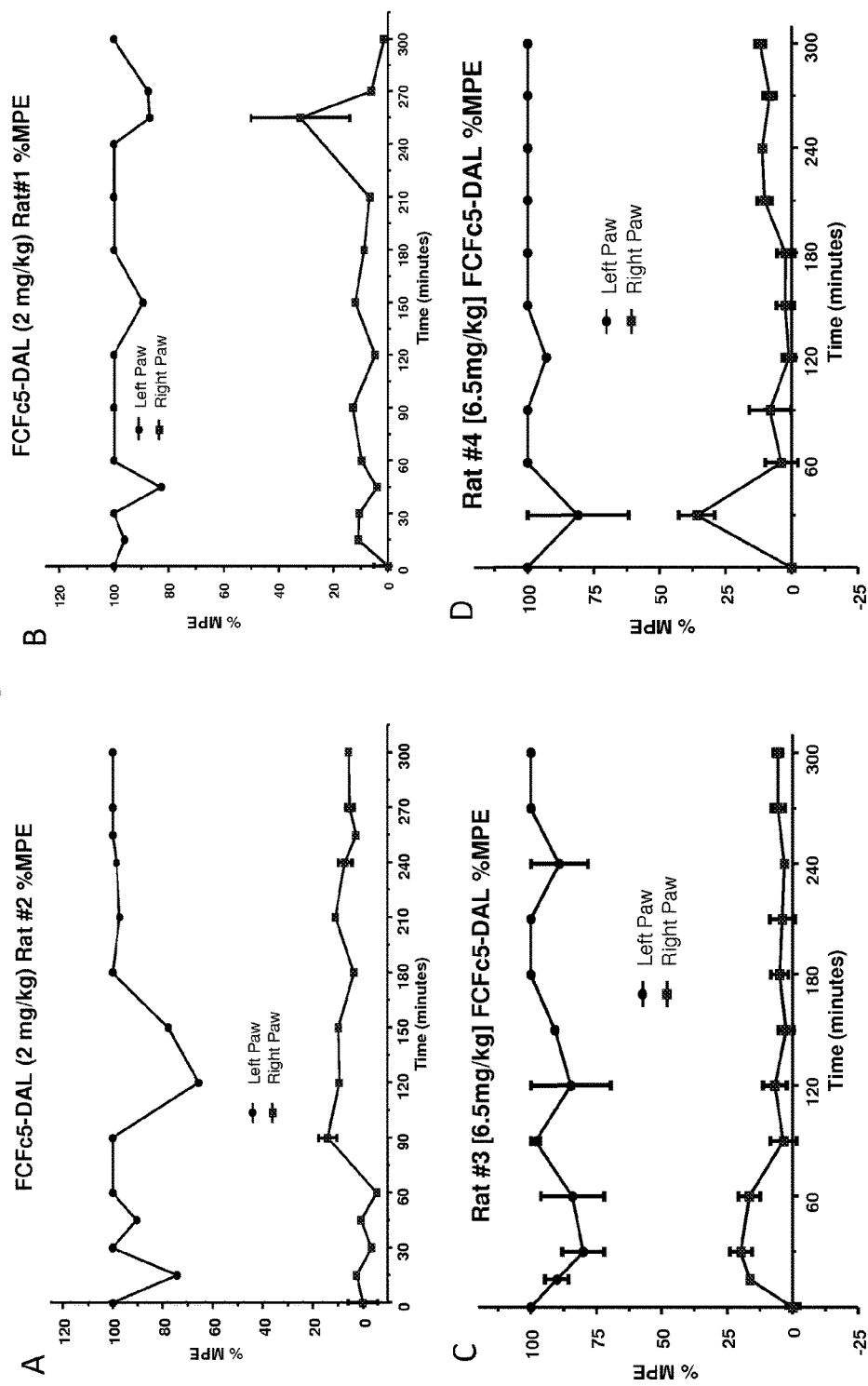
FIG. 6a-d. The efficacy of Fc-FC5-Dal was evaluated in the Hargreaves model. Rats were dosed IV at 2mpkat time 0 in Panel 6a and at time 0 and 2 h in panel 6B. In panels 6C and 6D each rat was dosed IV at 6.5 mpk at time 0.

Binding Affinity of FC5 Molecules for TMEM30A:

The binding affinity of each molecule was evaluated in separate Fluorescent Flow Cytometry assay using freshly isolated rat BBB endothelial cells, SV40 transformed rat BBB endothelial cells (Caram-Salas, N., Boileau, E., Farrington, G. K., Garber, E., Brunette, E., Abulrob, A., and Stanimirovic, D. *Methods in molecular biology* 763, ed. 2010, 383-401) and to Hek293 cells transiently transfected with the previously identified target TMEM30A. The binding curves to each cell line are shown in FIG. 4A-C, and the calculated affinity values are in Table III. The results show the binding of FC5Fc to primary rat BBB endothelial cells to have an affinity of 11 nM, whereas binding to the SV40 transformed cell line results in an EC50 value of 75 nM, about 7 fold weaker binding. Whereas binding to the rat TMEM30A transiently transformed Hek293 cell-line results in an affinity of around 1700 nM, nearly 170 fold weaker than the binding to the primary BBB endothelial cell line. These data show that the FC5-Fc has a substantial increase in apparent affinity over FC5 Vhh alone when measured by flow cytometry, suggesting that the FC5-Fc binds with bidentate avidity to cells expressing TMEM-30A.

Efficacy Evaluation in Animal Models:

To assess what affect FC5 Vhh domain dimerization would have on the ability of the molecule to function as a transporter to deliver a molecular payload across the BBB via RMT the activity of these molecules was evaluated in animal models. It is known that numerous factors can affect the efficiency of transport, for example it has been reported that decreasing the affinity of an anti-transferrin receptor antibody even several fold had a positive impact on the ability of the molecule to effectively undergo BBB transmigration (Yu, Y. J., Zhang, Y., Kenrick, M., Hoyte, K., Luk, W., Lu, Y., Atwal, J., Elliott, J. M., Prabhu, S., Watts, R. J., and Dennis, M. S. *Science translational medicine* 3(84), 84ra44). According to this concept, significant affinity enhancement upon Fc dimerization of the FC5 Vhh would be predicted to negatively impact the ability of FC5 Vhh to function as an effective BBB transport molecule. Therefore the potency of molecules to which neuroactive peptide had been linked, each molecule having a different FC5 valency, was evaluated in an in vivo model.

The Hargreaves model measures increased sensitivity to thermal pain induced by injection of Freud's adjuvant in a paw. The thermal pain can be suppressed upon binding of a six amino acid peptide Dalargin to the mu pain receptors expressed in the peri-aquaductal portion of the brain. Intravenously injected Dalargin is unable to cross BBB and does not result in pain suppression, however ICV injection allows Dalargin to diffuse to the mu receptors and block the mu receptors and thereby block pain. Thus intravenously injected Dalargin must be linked to a receptor mediated transporter to allow cross BBB transport and suppression of pain. To evaluate the transport of Dalargin mediated by FC5 containing molecules across the BBB the Hargreaves animal model was used to compare the potency of various molecular forms of FC5 Vhh linked to Dalargin. The negative control molecule for FC5-Dalargin was EG2-Dalargin and for FC5-Fc-Dalargin was Fc-FC5-Dalargin.

To insure the comparability of the positive and negative test articles FC5-Dal and EG2-Dal were characterized by mass spectrometry to show that the ratio of Dalargin peptides linked to each Vhh were comparable (Table I).

Prior to intravenous (IV) injection each molecule was initially tested by intracerebroventricular (ICV) injection as a positive control to insure all linked molecules are functionally active and able to induce pain suppression. Both negative control and positive test molecules would be expected to suppress pain upon ICV injection as the molecules are injected directly into the cerebral spinal fluid and are able to diffuse to and block the periacquiductal mu pain receptors. In all cases when evaluated by ICV injection FC5-Dal, EG2-Dal, FC5-Fc-Dal, Fc-FC5-Dal or Dalargin alone gave similar potency based on the amount of Dalargin delivered. Next each Dalargin labeled molecule and corresponding Dalargin labeled control protein were evaluated for efficacy upon IV administration. Initially, the efficacy of FC5-Dal versus the control (EG2-Dal) was compared. The results show full pain suppression similar to the level of suppression that can be observed with morphine alone was achieved (FIGS. 5*a* & *b*). It is interesting to note that three doses of FC5-Dal at 7.5 mg per kg (mpk) per dose as needed prior to observing the initial pain suppression. In addition the control group showed no suppression of pain even after animals were dosed similarly three times at 7.5 mg per kg (mpk). These data demonstrate and confirm that FC5 is able to function as a receptor mediated transporter, transporting Dalargin across the BBB into the brain parenchyma and allowing Dalargin to bind and block the mu pain receptors, whereas the control EG2-Dalargin showed no pain suppression. These data are summarized in Table IV.

The dimerized FC5 forms, FC5-Fc and Fc-FC5, demonstrated very different binding affinities for TMEM 30A on BBB endothelial cells (Table III). To determine if the enhanced affinity correlated with improved potency in the Hargreaves pain model, both FC5-Fc-dal and Fc-FC5-dal were evaluated for pain suppression. Following IV injection Fc-FC5-dal showed no efficacy (FIG. 6*a-d*), whereas FC5-Fc-dal (FIGS. 7*a* & 7*c*) was highly efficacious in pain suppression. In additional the negative control Fc-Dal showed no efficacy in vivo (FIGS. 7*b* & 7*d*). FC5-Fc showed efficacy in reducing pain within the first hour even with a single dose initially at 0.5 mpk, with an average of 50% MPE after the first 0.5 h. Comparing the potency of FC5-dal with FC5-Fc-dal results showed a single dose of FC5-dal at 21 mpk gave about the same level of pain suppression as FC5-Fc-Dal at 0.5 mpk. Based on the molar ratio of Dalargin injected the FC5Fc-Dal shows about an 80 fold greater potency than FC5-Dal in ability to suppress pain in the Hargreaves model. A second dose of FC5-Fc-Dal at 2.5 mpk was sufficient in one animal to give maximum possible pain suppression. The observed enhanced biological activity of the FC5-Fc-Dal, Fc-FC5-Dal and FC5-Dal observed in the Hargreaves pain model correlates the higher affinity and higher efficacy, of FC5-Fc as summarized in Table II.

In addition, similar efficacies for pain suppression can be achieved using other neuroactive peptides. For example Galanin a 29 amino acid 3.2 kD peptide linked to FC5 or FC5-Fc, with identical chemistry to that described above, suppressed chronic pain in the Hargreaves model. In contrast, Galanin linked to the Fc alone was unable to provide effective pain relief. The results for both the ICV positive control and IV injections are summarized in Table VI. To validate the activity of the linked Galanin to bind its cognate receptors GalR1 and GalR2 and suppress pain in both the negative control and test molecules all molecules were tested and shown to suppress pain after ICV injection (Table VI). When injected IV, only Galanin linked to the FC5 containing molecules, either FC5 or FC5-Fc were able to suppress pain in vivo. There was a significant difference in the dosing of Galanin linked to FC5 versus FC5-Fc required to reduce pain in the Hargreaves animal model. The Galanin- FC5 in a single dose of 6 mpk (Table VI) resulted in an 8% MPE, whereas a single dose of FC5-Fc-Gal resulted in a 45% MPE.

Intraperitoneal administration of pentylenetetrazol (PTZ) induces seizures in rats and has been used as a model of Eplileptic seizures (Chen, J. W.; Naylor, D. E.; Wasterlain, C. G. Advances in the pathophysiology of status epilepticus. *Acta Neurol. Scand. Suppl.*, 2007, 186, 7-15.; Werner, F. M.; Coveñas, R. Neuropeptides involved in schizophrenia, *Curr. Top. Neurochem.*, 2005, 4, 35-49.; Werner, F. M.; Coveñas, R. In: Focus on Neuropeptide Research, Coveñas, Mangas and Narváez, Eds.; Transworld Reasearch Network: Trivandrum, 2007; pp. 299-339; Werner, F. M.; Coveñas, R. Classical neurotransmiters and neuropeptides involved in major depression. *Int. J. Neurosci.*, 2010, 120, 455-70). It is known that neuroactive peptides such as Galanin and Neuropeptide Y impart protection from PTZ induced seizures (Mazarati 1998a; Mazarati, A M., Hohmann, J. G., Bacon, A, Liu, H., Sankar, R., Steiner, R. A, Wynick, D., et al. Modulation of hippocampal excitability and seizures by galanin. *The Journal of neuroscience: the official journal of the Society for Neuroscience*, 2000, 20(16), 6276-81.). Mazarati et al. (Mazarati A, Liu H, Soomets U, Sankar R, Shin D, Katsumori H, Langel U, Wasterlain CG Galanin modulation of seizures and seizure modulation of hippocampal galanin in animal models of status epilepticus. J Neurosci 1998, 18:10070-10077.). These studies showed depletion of Galanin from the rat hippocampus is associated with development of self-sustaining status epileticus. In addition, the injection of Galanin into the hippocampal region of the brain can suppress seizures (Mazarati A, Liu H, Soomets U, Sankar R, Shin D, Katsumori H, Langel U, Wasterlain CG Galanin modulation of seizures and seizure modulation of hippocampal galanin in animal models of status epilepticus. J Neurosci 1998, 18:10070-10077.; Mazarati A M, Halaszi E, Telegdy G Anticonvulsive effects of galanin administered into the central nervous system upon the picrotoxinkindled seizure syndrome in rats. Brain Res 1992, 589:164-166.). However, neuroactive peptides given intravenously cannot cross the BBB and have a brief half-life owing to their small size (Jain, Kamal and Batra. Trends Biotechnol. Vol 25. ed.: 2007:307-16, Batra, Jain, Wittel, Chauhan and Colcher. Curr Opin Biotechnol. Vol 13. ed.: 2002:603-8). The efficacy of Galanin in the PTZ model was evaluated by testing Galanin linked to both FC5, the single domain antibody, and to FC5-Fc. Although both constructs are expected to enhance BBB transport, the FC5-Fc construct was shown herein to have increased practical affinity due to avid binding to its putative target TMEM30A and to have a much longer half-life owing to increased size and Fc dependent recycling.

In the PTZ induced seizure model, the agent of interest is injected either IV or by direct hippocampal injection. The hippocampal injection delivers the agent directly to the site of action allowing Galanin to bind its cognate receptors and block seizure onset. In addition, direct hippocampal injection of each molecule serves as a positive control to show Galanin linked to each molecule, Fc, FC5 or FC5-Fc, retains seizure suppressive activity. Doses of each molecule administered were varied to give near molar equivalent Galanin doses. For the positive control study, male Wistar rats (4-6 weeks old) received an intrahippocampal injection of one of the following: Valproic acid, Gal-Cya or FC5-Gal in a final volume of 5 uL, followed 15 min later with an IP injection of 50 mpk PTZ to induce the seizures.

Figure 7:
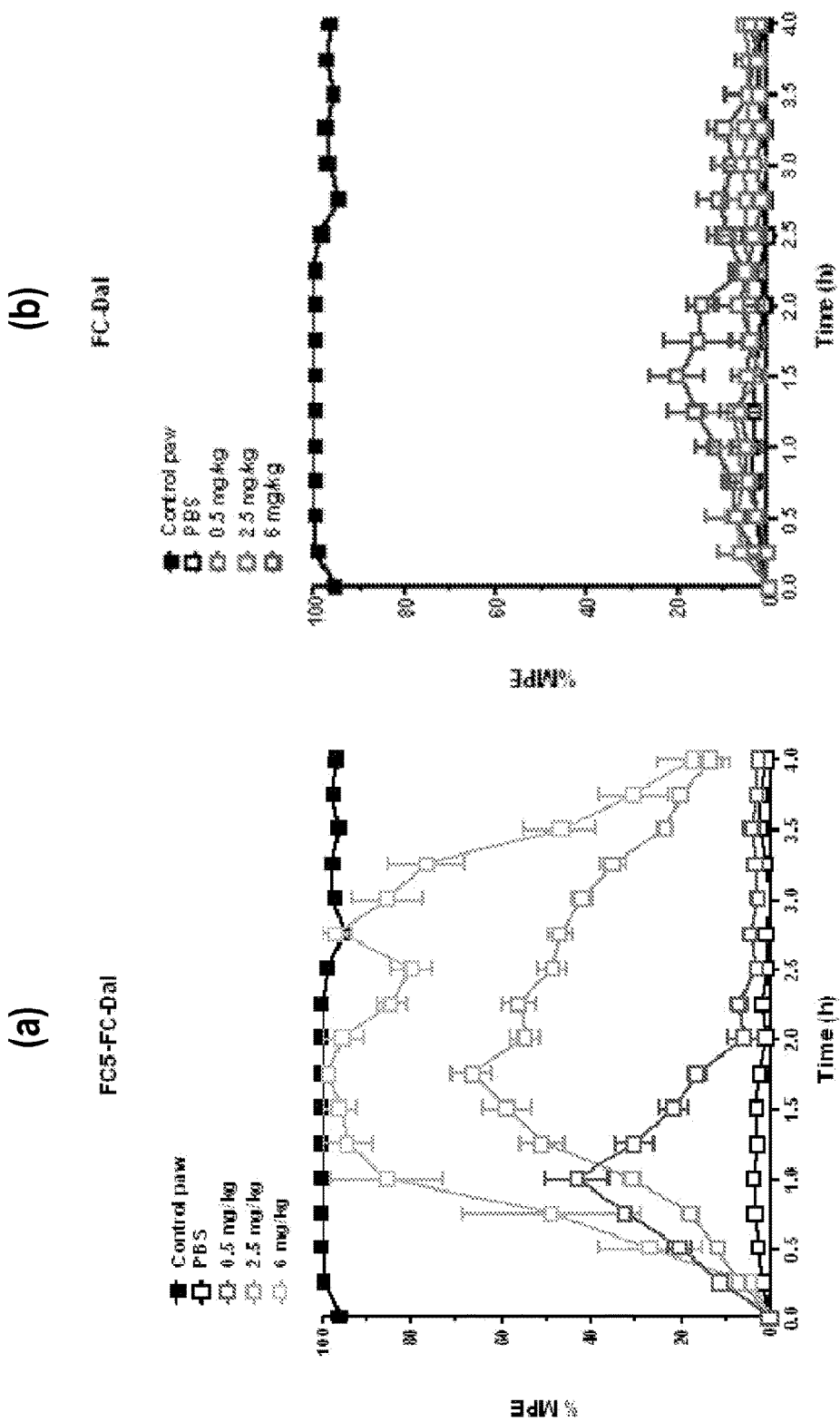
FIG. 7a-d. The efficacy in the Hargreaves model of FC5-Fc-Dal was compared with a negative control Fc-Dal.
Figure 7:
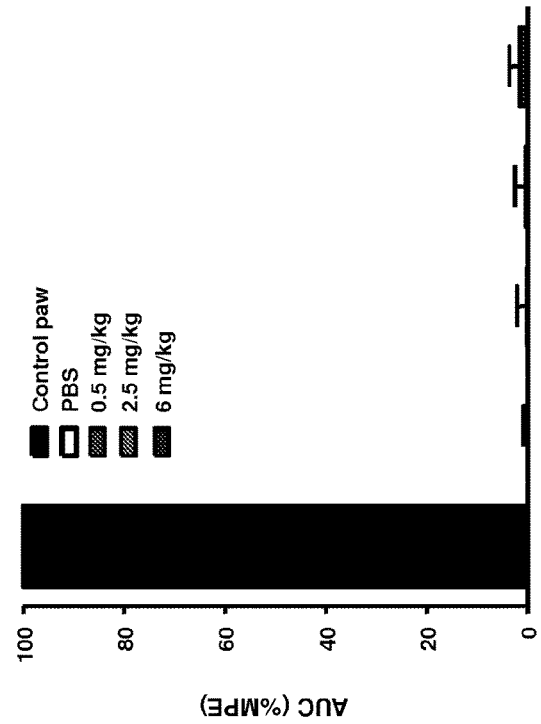
Figure 7:
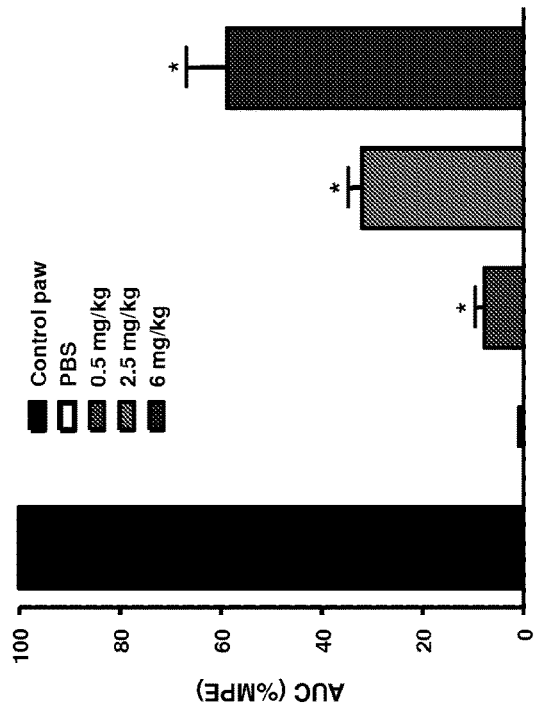

To evaluate the effectiveness of Galanin linked to FC5, FC5-Fc or Fc to cross the BBB, each of these molecules was injected systemically as detailed in FIGS. 7A and 7B. For the systemic study, rats received 1, 2 or 3 intravenous injections (through tail vein) of Gal-Cya or FC5-Gal, or a single dose of either FC5-Fc-Gal or Fc-Gal. In each case following the IP PTZ injection at a dose of 50 mpk was administered intraperitoneally and the rat's movements were recorded for 30 minutes.

All recorded movements were then reviewed and the time to onset of seizures and seizure duration times are measured by an unbiased investigator for each of three characteristic behavioral changes: first myoclonic jerk (FMJ; which is characterized by ear, head and shoulder twitches), first clonic seizure (FCJ; which is characterized by minimal seizures, clonus of the head muscles and forelimbs, involuntary movements of whole body and jumping movements with righting reflex) and first tonic generalized extension (TGE; which is characterized by the loss of righting ability, flexion or extension of fore- and hindlimbs and clonus of the whole body).

Table VIIa shows the results for the intrahippocampal injections of each molecule. IP injection of the 50 mpk PTZ resulted in rapid onset of each type of seizure, myoclonic, clonic and generalized tonic with very rapid progression from the least serious FMJ to the most serious seizure form generalized tonic. Valproic acid a small molecule known to partially suppress PTZ induced seizure onset (Pollack G. M., Shen D. D. *J Pharmacol Methods*. (1985) April; 13(2):135-46.) significantly delayed all three seizure types, but did not completely prevent seizure onset, with about a 100 second delay in onset of the myoclonic and clonic seizures observed. Intrahippocampal injection of Galanin alone or linked to FC5 resulted in significant delay of the myoclonic seizures and complete prevention of the more serious clonic and generalized tonic seizures.

The results obtained with intravenous dosing of each molecule are shown in Table VIIb. PTZ leads to rapid onset of each seizure type and Valproic acid at 11.2 mpk IV dosing suppresses the onset of the myoclonic and clonic seizures. Intavenous Galanin and Galanin-Fc, a short and long half-life version of the neuroactive peptide, resulted in no or very slight delay of seizure onset, respectively. FC5-galanin dosed at 6 mpk, 1 h prior to the PTZ dosing resulted in significant delay of the myoclonic seizure and complete suppression of the clonic and generalized clonic seizures. A single dose of FC5-Fc-Galanin two hours prior to the PTZ dosing also resulted in a significant delay of the myoclonic seizure and complete suppression of the clonic and generalized clonic seizures.

Several conclusions can be drawn from these results. Galanin linked to FC5, Fc or FC5-Fc retains equivalent activity as shown when dosed ICV in the Hargreaves model (Tables IV & V), in addition Table VIIa shows FC5-galanin showed equivalent activity on a molar basis to Galanin alone when injected into the hippocampus of rats in the PTZ seizure model. In contrast, Galanin alone or as a long lived molecule attached to hFc molecule does not effectively cross the blood-brain barrier and suppress PTZ induced seizures. Only when attached to FC5, either as FC5-Galanin or as FC5-Fc-Galanin, is Galanin able to cross the BBB and effectively delay and suppress PTZ induced seizures. Galanin linked to FC5-Fc is much more effective than Galanin linked to FC5 alone in reduction of seizures based on a molar dosing comparison; specifically, it is at least sixteen fold more potent. In addition, FC5-Fc Galanin showed a greater delay in time to onset of the first myoclonic seizure when compared FC5-Galanin. These results indicate that the improved half-life and practical affinity increase of the FC5-Fc for its target improves cross BBB delivery of Galanin and results in more effective seizure reduction in the PTZ seizure model than FC5 Galanin.

TABLE I

Characterization of expressed and purified molecules.

| Molecule plasmid | FC5[1] (EAG2333) | FC5-Fc[2] (EAG2345) | Fc-FC5[2] (EAG2304) | Fc |
|---|---|---|---|---|
| Calculated Mwt (Daltons) | 15,375 | 78,725 | 78,924 | 51,896 |
| Endotoxin (EU/mg) | <1 | <1 | <1 | <1 |
| LS Mwt (Daltons) | 16,860 | 77,530 | 78,950 | 57,800 |
| Purity % area of peak in analytical SEC | 99.7 | 98.9 | 95.0 | 99.7 |
| Avg linked Dalargin peptides[3] | 1.5 | 1.5 | 1.5 | 1.0 |

[1]contains myc tag EQKLISEEDL (SEQ ID NO: 13), C-termini (1202 mwt), C-terminal His tag 5H (SEQ ID NO: 14)
[2]Fc domains are human IgG1 and agly (all Fc domains contain a T299A point mutation in the hIgG sequence to eliminate Fc N-glycosylation)
[3]evaluated by MS, to determine the average number of Dalargins covalently to the FC5-Fc domains.

TABLE II

Pharmacokinetic half-life determinations of FC5 domains fused to a hFc.

| Assay format | FC5-Fc | | Fc-FC5 | | hIgG1 |
|---|---|---|---|---|---|
| | Fluorescence | ELISA | Fluorescence | Fluorescence | ELISA |
| Beta-phase half life (h) | 39.4 | 35.7 | 38.6 | 43.5 | 48 |

Half-life was determined by ELISA detection of the human Fc from rat serum or with AL680 labeled molecules and the fluorescence determined from the sera. No difference was observed between molecules in which the half-life was determined by fluorescence versus ELISA. Molecules were injected intraperitoneal at 3 mpk.

TABLE III

Summary of the binding affinities and relative efficacy of FC5-Dal, FC5-Fc-Dal and Fc-FC5-Dal in the Hargreaves model, showing the correlation of efficacy and affinity to BBB endothelial cells.

| | Affinity (nM) | | |
|---|---|---|---|
| Molecule | FC5 | FC5-Fc | Fc-FC5 |
| Primary rat BBB EC | >2000 | 11 | 1700 |
| SV-ARBEC | | 75 | ND |
| Rat Aortic endothelial | | 1700 | |
| Fold potency compared to FC5-Dal in Hargreaves model | 1 | 80 | <0.1 |

TABLE IV

Summary of chronic pain suppression in the Hargreaves model by Dalargin alone or linked to FC5.

| | ICV | | IV | |
|---|---|---|---|---|
| molecule | Dose (ug) | % MPE | Dose (mg/kg) | % MPE |
| PBS | 5 | 0 ± 0.8 | 800 (µL) | 0 ± 0.6 |
| Dalargin | 2 | 35 ± 1 | 0.34 × 3 inj | 0.3 ± 0.3 |
| FC5 | 69.75 | 0 ± 2 | 7 × 3 inj | 1.9 ± 0.3 |
| EG2 | 69.75 | 0 ± 2 | 7 × 3 inj | 0 ± 1.3 |
| A20.1 | | | 7.84 × 3 inj | 2.2 ± 0.3 |
| FC5-Dalargin | 74.4 | 47 ± 2 | 7 × 3 inj | 41 ± 0.5 |
| EG2-Dalargin | 74.4 | 31 ± 1 | 7 × 3 inj | 2.0 ± 0 |
| A20.1-Dalargin | | | 2.49 × 3 inj | 3.1 ± 0 |
| FC5 + Dalargin | | | (0.65 ug + 7 mg/Kg) × 3 inj | 0 ± 1.6 |

Chronic pain suppression is expressed as the percentage of maximum possible effect (% MPE). The value is based on the area under the curve for pain suppressed animal relative to the contralateral control paw over the time frame of measurement. The efficacy of molecules injected either ICV or IV is shown as a percent of maximum possible effect (% MPE) in the Hargreaves model. A20.1 and EG2 are single domain antibodies unrelated to FC5, that have no apparent affinity for BBB endothelial cells. Dose in mpk for intravenous (IV) dosing values are indicated as per injection followed by the number of injections.

TABLE V

Summary of chronic pain suppression in the Hargreaves model by Dalargin linked to Fc or Dalargin linked to FC5-Fc.

| | ICV | | IV | |
|---|---|---|---|---|
| molecule | Dose (ug) | % MPE | Dose (mg/kg) | % MPE |
| FC5-Fc-Dal | 11.5 | 43 ± 3 | 6 | 46 ± 2 |
| Fc Dal | 9.3 | 55 ± 2 | 6 | 5 ± 2 |
| FC5-Fc + FC5-Fc-Dal | | | 2.5 + 6 | 32 ± 7 |

In the second experiment an IV dose of unlinked FC5-Fc was injected IV prior to addition FC5-Fc-Dal at the concentrations indicated.

TABLE VI

Chronic pain suppression in the Hargreaves model by Galanin linked to either Fc, FC5-Fc or FC5.

| | ICV | | IV | |
|---|---|---|---|---|
| molecule | Dose (ug) | % MPE | (mg/kg) | % MPE |
| Galanin | 2 | 54 ± 1 | 1 | 0 ± 1 |
| Fc-Gal | 11.2 | 49 ± 1 | 6 | 2 ± 1 |
| FC5-Gal | 10.87 | 49 ± 2 | 6 | 8 ± 1 |
| FC5-Fc-Gal | 11.4 | 49 ± 2 | 6 | 45 ± 2 |

In the case of multiple doses for FC5-Gal, doses were spaced 1 h apart. In the third experiment an IV dose of unlinked FC5-Fc was injected IV prior to addition FC5-Fc-Dal at the concentrations indicated.

TABLE VII

Comparison of time to seizure onset using hippocampal injection (a) or IV injection (b) in the rat PTZ model a) Hippocampal injection.

| molecule | Dose (ug) | Myolconic (sec) | Clonic | Tonic Generalized |
|---|---|---|---|---|
| PTZ only | 50 mg/kg | 0 ± 2 | 0 ± 6 | 0 ± 0.5 |
| Valproic acid | 11.2 | 100 ± 6 | 100 ± 9 | 2 ± 1 |
| Galanin | 1.82 | 104 ± 0 | prevented | prevented |
| FC5-Galanin | 11.9 | 82 ± 4 | prevented | prevented | b) Intravenous injection.

| molecule | Dose (mg/kg) | Myolconic (sec) | Clonic | Tonic Generalized |
|---|---|---|---|---|
| PTZ only | 50 mg/kg | 0 ± 1 | 0 ± 3 | 0 ± 0.5 |
| Valproic acid | 11.2 | 100 ± 3 | 100 ± 3 | 100 ± 0 |
| Galanin | 1 × 2 inj | 0.5 ± 5 | 0 ± 2 | 2 ± 4 |
| Fc-Gal | 6 | 2 ± 1 | 18 ± 2 | 17 ± 2 |
| FC5-Galanin | 6 × 3 inj | 47 ± 3 | prevented | prevented |
| FC5-Fc-Galanin | 6 | 101 ± 28 | prevented | prevented |

Following IP dosing of rats with PTZ the time to onset for each type of seizure indicated below; FMJ, FCJ and TGE was tested. The seizure types are described in more detail supra. (a) PTZ administered IP establishes the control time to each seizure type. Hippocampal injection of Valproic Acid, Galanin or FC5-Galanin prior to IP injection of PTZ establishes the maximum effect each of these molecules can have on the time to each seizure type. (b) IV dosing of Valproic Acid, the positive control, Galanin (1×3 injection doses, each dose 1 h apart completed 45 min prior to PTZ dosing) or FC5-Galanin (1×3 doses, each dose 1 h apart completed 45 min prior to PTZ dosing), FC5-Fc-Gal or Fc-Gal were both dosed 2 h prior to IP injection of PTZ measures the effect each of these molecules can have upon IV dosing. Fc-Gal serves as the negative control as the molecule lacks the FC5 F(ab) fragment, but has a similar in vivo PK to FC5-Fc.

```
Seg1: The sequence of FC5-agly (T299A)hFc. (pEAG2345)
DVQLQASGGGLVQAGGSLRLSCAASGFKITHYTMGWFRQAPGKEREFVSRITW

GGDNTFYSNSVKGRFTISRDNAKNTVYLQMNSLKPEDTADYYCAAGSTSTATP

LRVDYWGKGTQVTVSSAEPKSCDKTHTCPPCPAPELLGGPSVFLFPPKPKDTLM

ISRTPEVTCVVVDVSHEDPEVKFNWYVDGVEVHNAKTKPREEQYNSAYRVVSV

LTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVD

KSRWQQGNVFSCSVMHEALHNHYTQKSLSLSPGK (SEQ ID NO: 1)

Seq2: The sequence of agly (T299A) hFc-FC5. (pEAG2403)
EPKSSDKTHTCPPCPAPELLGGPSVFLFPPKPKDTLMISRTPEVTCVVVDVSHEDP

EVKFNWYVDGVEVHNAKTKPREEQYNSAYRVVSVLTVLHQDWLNGKEYKCK

VSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEA

LHNHYTQKSLSLSPGGGGGSDVQLQASGGGLVQAGGSLRLSCAASGFKITHYT

MGWFRQAPGKEREFVSRITWGGDNTFYSNSVKGRFTISRDNAKNTVYLQMNSL

KPEDTADYYCAAGSTSTATPLRVDYWGKGTQVTVSS (SEQ ID NO: 2)

Seq3: The sequence of scrambled FC5-agly (T299A)hFc (pYL605)
EPKSSDKTHTCPPCPAPELLGGPSVFLFPPKPKDTLMISRTPEVTCVVVDVSHEDP

EVKFNWYVDGVEVHNAKTKPREEQYNSAYRVVSVLTVLHQDWLNGKEYKCK

VSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEA

LHNHYTQKSLSLSPGGGGGSDVQLQASGGGLVQAGGSLRLSCAASGFKITHYT

MGWFRQAPGKEREFVSRITWGGDNTFYSNSVKGRFTISRDNAKNTVYLQMNSL

KPEDTADYYCAADAGSTGSYGSFDYWGKGTQVTVSS (SEQ ID NO: 3)
```

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A binding molecule comprising at least one pharmacologically active agent and at least one binding site that binds to TMEM30A (SEQ ID NO: 9), wherein the at least one binding site that binds to TMEM30A is fused i) directly or ii) via an intervening amino acid sequence to the N-terminus of an Fc moiety.

2. The binding molecule of claim 1, wherein the at least one binding site that binds to TMEM30A comprises the FC5 amino acid sequence (SEQ ID NO: 10).

3. The binding molecule of claim 1, wherein the at least one binding site that binds to TMEM30A consists of the FC5 amino acid sequence.

4. The binding molecule of claim 1, wherein the binding molecule comprises at least three binding sites that bind to TMEM30A.

5. The binding molecule of claim 1, wherein the binding molecule comprises at least four binding sites that bind to TMEM30A.

6. The binding molecule of claim 1, wherein the at least one binding site that binds to TMEM30A is fused directly to the Fc moiety.

7. The binding molecule of claim 1, wherein the at least one binding site that binds to TMEM30A is fused to the Fc moiety via an intervening amino acid sequence comprising a peptide linker.

8. The binding molecule of claim 1, wherein the at least one binding site that binds to TMEM30A is fused to the N terminus of an scFc molecule.

9. The binding molecule of claim 1, wherein the at least one pharmacologically active agent is fused to the C-terminus of the Fc moiety.

10. The binding molecule of claim 1, wherein the at least one pharmacologically active agent is a polypeptide.

11. The binding molecule of claim 1, wherein the at least one pharmacologically active agent is fused to the at least one binding site that binds to TMEM30A.

12. The binding molecule of claim 1, wherein the at least one pharmacologically active agent is covalently linked to the at least one binding site that binds to TMEM30A.

13. The binding molecule of claim 1, wherein at least two binding sites that binds to TMEM30A are fused to the N terminus of a VH domain and a VL domain of an intact antibody molecule.

14. The binding molecule of claim 1, wherein the pharmacologically active agent comprises an agent that is selected from the group consisting of a neuroactive peptide, a cytokine, and a variable region of an antibody that binds to a target in the central nervous system.

15. The binding molecule of claim 1, wherein the binding molecule comprises at least two binding sites that bind to TMEM30A.

16. The binding molecule of claim 15, wherein the two binding sites that bind to TMEM30A are each fused to the N terminus of a first and a second Fc moiety of a complete Fc region, respectively, via an amino acid sequence comprising a peptide linker, wherein the first and the second Fc moiety are different from each other.

17. The binding molecule of claim 10, wherein the polypeptide comprises an antigen binding site.

18. The binding molecule of claim 17, wherein the antigen binding site is derived from a non-TMEM30A binding antibody.

19. The binding molecule of claim 18, wherein the pharmacologically active agent is selected from the group consisting of an scFv molecule, a diabody, a Fab molecule, and a single domain antibody.

20. The binding molecule of claim 1, wherein the at least one binding site that binds to TMEM30A is fused via an intervening amino acid sequence comprising the VL domain of an antibody molecule.

21. The binding molecule of claim 20, wherein the at least one binding site that binds to TMEM30A is fused to the N terminus of a VL domain of an intact antibody molecule.

22. The binding molecule of claim 1, wherein the at least one binding site that binds to TMEM30A is fused via an intervening amino acid sequence comprising the VH domain of an antibody molecule.

23. The binding molecule of claim 22, wherein the at least one binding site that binds to TMEM30A is fused to the N terminus of a VH domain of an intact antibody molecule.

24. The binding molecule of claim 22, wherein the intervening amino acid sequence further comprises a peptide linker.

25. The binding molecule of claim 1, wherein the pharmacologically active agent is an agent that is useful in treating or ameliorating the effects of a neurological disease.

26. A method of treating a neurological disorder, comprising administering the binding molecule of claim 25 to a subject in need thereof.

27. The method of claim 26, wherein the neurological disorder is a storage disorder, chronic pain, epilepsy, multiple sclerosis, a proteinopathy, or a demyelinating disorder.

28. A binding molecule comprising:
at least one pharmacologically active agent;
at least two single domain antibodies that bind to TMEM30A (SEQ ID NO:9); and
an Fc region comprising a first Fc moiety and a second Fc moiety,
wherein the at least two single domain antibodies that bind to TMEM30A are each fused to the N terminus of the first Fc moiety and the second Fc moiety, respectively, either directly or via an amino acid sequence comprising a peptide linker.

29. The binding molecule of claim 28, wherein the first Fc moiety and the second Fc moiety each comprise a CH2 domain and a CH3 domain.

30. The binding molecule of claim 28, wherein the first Fc moiety and the second Fc moiety each comprise a hinge region, a CH2 domain, and a CH3 domain.

31. The binding molecule of claim 28, wherein the Fc region is from an IgG antibody.

32. The binding molecule of claim 28, wherein the at least two single domain antibodies that bind to TMEM30A comprise the FC5 amino acid sequence (SEQ ID NO:10).

33. The binding molecule of claim 28, wherein the at least two single domain antibodies that bind to TMEM30A consist of the FC5 amino acid sequence (SEQ ID NO:10).

34. The binding molecule of claim 28, wherein the Fc region is from an IgG antibody and the first Fc moiety and the second Fc moiety each comprise a hinge region, a CH2 domain, and a CH3 domain, and wherein the at least two single domain antibodies that bind to TMEM30A comprise the FC5 amino acid sequence (SEQ ID NO:10).

35. The binding molecule of claim 28, wherein the Fc region is from an IgG antibody and the first Fc moiety and the second Fc moiety each comprise a hinge region, a CH2 domain, and a CH3 domain, and wherein the at least two single domain antibodies that bind to TMEM30A consist of the FC5 amino acid sequence (SEQ ID NO:10).

36. The binding molecule of claim 28, wherein the at least one pharmacologically active agent is selected from the group consisting of an antibody, an scFv molecule, a diabody, a Fab molecule, a Fab' molecule, a F(ab')2 molecule, a Fv molecule, and a single domain antibody.

37. The binding molecule of claim 28, wherein the at least two single domain antibodies that bind to TMEM30A are each fused directly to the N terminus of the first Fc moiety and the second Fc moiety, respectively.

38. The binding molecule of claim 28, wherein the at least one pharmacologically active agent is fused to the C-terminus of the first Fc moiety or the second Fc moiety.

39. The binding molecule of claim 28, comprising SEQ ID NO:1.

40. A binding molecule consisting of:
a pharmacologically active agent;
two single domain antibodies that bind to TMEM30A (SEQ ID NO:9); and
an Fc region comprising a first Fc moiety and a second Fc moiety,
wherein the at least two single domain antibodies that bind to TMEM30A are each fused to the N terminus of the first Fc moiety and the second Fc moiety, respectively, either directly or via an amino acid sequence comprising a peptide linker.

41. The binding molecule of claim 40, wherein the at least two single domain antibodies that bind to TMEM30A comprise the FC5 amino acid sequence (SEQ ID NO:10).

42. The binding molecule of claim 40, wherein the at least two single domain antibodies that bind to TMEM30A consist of the FC5 amino acid sequence (SEQ ID NO:10).

* * * * *